(12) United States Patent
Gardarsson et al.

(10) Patent No.: US 12,049,477 B2
(45) Date of Patent: Jul. 30, 2024

(54) AZITHROMYCIN DERIVATIVES WITH EPITHELIAL BARRIER ENHANCEMENT PROPERTIES

(71) Applicant: EpiEndo Pharmaceuticals ehf, Seltjarnarnes (IS)

(72) Inventors: Fridrik Runar Gardarsson, Seltjarnarnes (IS); Fredrik Lehmann, Uppsala (SE); Peter Teodorovic, Uppsala (SE)

(73) Assignee: EPIENDO PHARMACEUTICALS EHF., Reykjavik (IS)

( * ) Notice: Subject to any disclaimer, the term of this patent is extended or adjusted under 35 U.S.C. 154(b) by 171 days.

(21) Appl. No.: 17/551,223

(22) Filed: Dec. 15, 2021

(65) Prior Publication Data
US 2022/0106349 A1 Apr. 7, 2022

Related U.S. Application Data

(60) Continuation of application No. 16/904,593, filed on Jun. 18, 2020, now Pat. No. 11,236,120, which is a division of application No. 15/777,223, filed as application No. PCT/EP2016/078360 on Nov. 21, 2016, now Pat. No. 10,723,752.

(30) Foreign Application Priority Data

Nov. 19, 2015 (GB) .................... 1520419

(51) Int. Cl.
| C07H 17/00 | (2006.01) |
| A61K 31/7048 | (2006.01) |
| A61P 11/00 | (2006.01) |
| C07H 17/08 | (2006.01) |

(52) U.S. Cl.
CPC ......... *C07H 17/00* (2013.01); *A61K 31/7048* (2013.01); *A61P 11/00* (2018.01); *C07H 17/08* (2013.01)

(58) Field of Classification Search
CPC .... C07H 17/00; C07H 17/08; A61K 31/7048; A61K 31/706; A61P 11/00–16; A61P 31/04
See application file for complete search history.

(56) References Cited

U.S. PATENT DOCUMENTS

| 2008/0234211 A1 | 9/2008 | Culic et al. |
| 2009/0076253 A1 | 3/2009 | Kashimura et al. |
| 2011/0028417 A1 | 2/2011 | Gutke et al. |
| 2018/0354981 A1 | 12/2018 | Gardarsson et al. |
| 2020/0317710 A1 | 10/2020 | Gardarsson et al. |

FOREIGN PATENT DOCUMENTS

| CN | 1837225 A | 9/2006 |
| CN | 101074251 A | 11/2007 |
| WO | 02/055531 A1 | 7/2002 |
| WO | 03/070174 A2 | 8/2003 |
| WO | 2004/005310 A2 | 1/2004 |
| WO | 2004039821 A1 | 5/2004 |
| WO | 2006/077501 A2 | 7/2006 |
| WO | 2006/087644 A2 | 8/2006 |
| WO | 2007129646 A1 | 11/2007 |
| WO | 2009/006403 A2 | 1/2009 |
| WO | 2010086351 A1 | 8/2010 |
| WO | 2012051126 A1 | 4/2012 |
| WO | 2012/131396 A1 | 10/2012 |
| WO | 2013/148874 A1 | 10/2013 |
| WO | 2014/166503 A1 | 10/2014 |

OTHER PUBLICATIONS

International Search Report and Written Opinion issued in corresponding International Patent Application No. PCT/EP2016/078360 dated Apr. 5, 2017 (9 pages).
Search Report issued in corresponding United Kingdom Patent Application No. GB1520419.1 dated Sep. 9, 2016 (5 pages).
Asgrimsson et al., "Novel Effects of Azithromycin on Tight Junction Proteins in Human Airway Epithelia," Antimicrobial Agents and Chemotherapy, vol. 50, No. 5, 2006, pp. 1805-1812.
Mishra et al., "PAMAM dendrimer-azithromycin conjugate nanodevices for the treatment of Chlamydia trachomatis infections," Nanomedicine: Nanotechnology, Biology and Medicine, vol. 7, No. 6, 2011, pp. 935-944.
Presland et al., "Transfer of Advances in Sciences into Dental Education-Making Sense of the Epithelial Barrier: What Molecular Biology and Genetics Tell Us About the Functions of Oral Mucosal and Epidermal Tissues," Journal of Dental Education, vol. 66, No. 4, 2002, pp. 564-574.
Stepanic et al., "Modeling cellular pharmacokinetics of 14- and 15-membered macrolides with physicochemical properties," Journal of Medicinal Chemistry, American Chemical Society, US, vol. 54, No. 3, 2011, pp. 719-733.
Yan et al., "Synthesis and Antibacterial Activity of Novel 3-O-descladinosylazithromycin derivatives," European Journal of Medicinal Chemistry, 2016, pp. 1-11.
Zhang et al., "Synthesis and antimicrobial activity of novel 3-O-carbamoyl derivatives of clarithromycin and 11, 12-cyclic carbonate azithromycin," European Journal of Medicinal Chemistry, Editions of Scientifique Elsevier, Paris, FR, vol. 45, No. 3, 2010, pp. 915-922.

(Continued)

*Primary Examiner* — Leigh C Maier
(74) *Attorney, Agent, or Firm* — Kilyk & Bowersox, P.L.L.C.

(57) ABSTRACT

The invention provides novel compounds that are derivatives of Azithromycin and that have been found by the current inventors to have low antimicrobial activity but significant epithelial barrier enhancement properties. The invention further provides use of the compounds as a medicament, in particular in the treatment or prophylaxis of a disease or condition that is caused by a defect in epithelial cells or tissue, or a disease or condition that benefits from enhancement or restoration of epithelial barrier function, for example diseases of the respiratory tract.

12 Claims, 1 Drawing Sheet

(56) References Cited

OTHER PUBLICATIONS

Slater et al., "The differential effects of azithromycin on the airway epithelium in vitro and in vivo," Physiological Reports, vol. 4 No. 18, 2016, pp. 1-15.
International Preliminary Report on Patentability issued in corresponding International Patent Application No. PCT/EP2016/078360 dated Oct. 20, 2017 (29 pages).
Office Action issued in corresponding Japanese Patent Application No. 2021-019109 dated Feb. 7, 2022 (English translation only) (7 pages).
Extended European Search Report issued in corresponding European Patent Application No. 20172534.8 dated Jul. 7, 2020 (11 pages).
Starcevic et al, "Novel hybrid molecules based on 15-membered azalide as potential antimalarial agents," European Journal of Medicinal Chemistry, 2012, vol. 49, pp. 365-378.
Moldoveanu et al, "Inflammatory mechanisms in the lung," Journal of Inflammation Research, 2009, vol. 2, pp. 1-11.
Office Action issued in corresponding Chinese Patent Application No. 202210535850.6 dated Sep. 29, 2023 (English translation only) (14 pages).
Oyelere et al., "Non-Peptide Macrocyclic Histone Deacetylase Inhibitors," Journal of Medicinal Chemistry, 2009, vol. 52, No. 2, pp. 456-468.
STN Search Record dated Aug. 13, 2010 (4 pages).

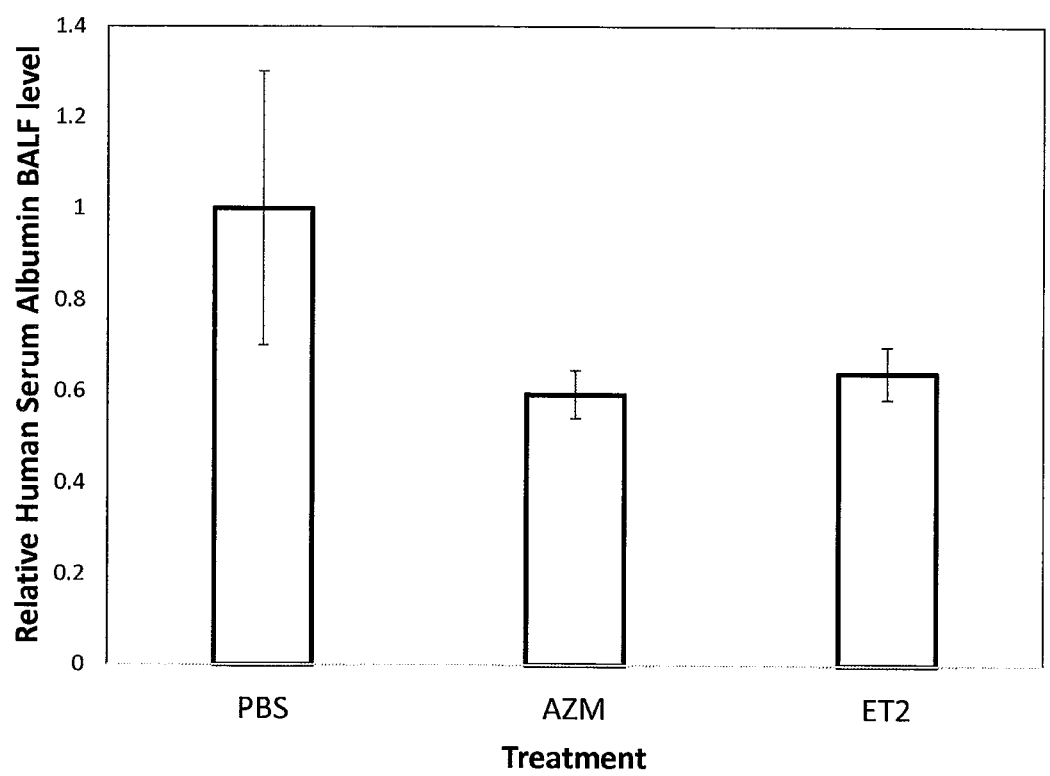

AZITHROMYCIN DERIVATIVES WITH EPITHELIAL BARRIER ENHANCEMENT PROPERTIES

This application is a continuation of U.S. patent application Ser. No. 16/904,593 filed Jun. 18, 2020 which in turn is a divisional of U.S. patent application Ser. No. 15/777,223 filed May 18, 2018, which in turn is a National Stage Application of PCT/EP2016/078360, filed Nov. 21, 2016, which claims priority to United Kingdom Patent Application No. 1520419.1, filed Nov. 19, 2015.

FIELD OF THE INVENTION

The current invention relates to macrolide derivatives with especially beneficial pharmacological properties. The compounds find use in the treatment of various conditions, including conditions of the respiratory tract, for example asthma, COPD, diffuse panbronchiolitis (DPB) and cystic fibrosis (CF).

BACKGROUND

Macrolides have a range of physiological activities. The majority of macrolides have an antimicrobial effect as part of their therapeutic mode of action. The macrolides are not only classified in terms of activity but also based on structure. Erythromycin, the original naturally occurring macrolide, has a 14-membered macrolactone as a backbone. The 12-, 13-, 15- and 16-membered macrolides are mostly modified derivatives of erythromycin as well as the closely related ketolides, which are broad spectrum antimicrobials.

Many macrolides exhibit a range of disease modifying activities in various diseases of seemingly unrelated aetiology. In addition to antimicrobial activity, some macrolides have been proposed to possess alternative "non-antimicrobial" effects. Some of those effects have been proposed to manifest themselves in a disease modifying mode of action in humans that is primarily anti-inflammatory or immunomodulatory (Kanoh, S. and Rubin B.K., Mechanisms of Action and Clinical Application of Macrolides as Immunomodulatory Medications, *Clinical Microbiology Reviews*, 2010, 23(3), 590-615). The term "Immunolides" has been used to describe macrolide compounds that have selective immunomodulatory effects (see Fecik et al., *Current Opinion in Drug Discovery and Development*, 2005, 8(6), 741-747).

In at least two double blinded clinical trials azithromycin ("Azm") has been shown to reduce the hospitalisation rate and disease related exacerbations by 30% in patients with COPD (see Uzun et al., Lancet Respiratory Medicine, 2014, 2(5), 361-368 and Albert et al., *New England Journal of Medicine*, 2011, 365(8), 689-698). Azm has also been shown to increase host defence against *P. aeruginosa* as well as increasing transepithelial resistance ("TER") in epithelial cells in vitro ALI culture and increases cellular processing of tight junctions. Erythromycin and penicillin have been found not to exhibit similar effects, (see Asgrimsson V et al (2006) Novel effects of azithromycin on tight junction proteins in human airway epithelia, *Antimicrob Agents Chemother*, 50: 1805-1812 and Halldorsson S et al. (2010) Azithromycin Maintains Airway Epithelial Integrity During *Pseudomonas aeruginosa* Infection. *Am J Respir Cell Mol Biol* 2010, 42(1), 62-68.).

TER is also known as TEER ("transepithelial electrical resistance"), and it is a measure of the electrical impendence of a cell layer. It is used as an indicator of formed and functional tight junctions, see, for example, Rezaee F and Georas S N, 2014, *Am J Respir Cell Mol Biol* 857-869. Increased TER is a parameter of good barrier properties and is associated with healthy polarised epithelial tissue whilst diseased or poorly-effective epithelial tissue is associated with poorer barrier function (see, for example, Marchiando et al., *Annu. Rev. Pathol. Mech. Dis.*, 2010, 5, 119-144), and higher permeability, and hence higher permeability.

Over-use of antibiotics is one of the causes of the rise of antibiotic-resistant strains of bacteria. The use of macrolides in the treatment of conditions other than bacterial infections has thus been limited by the need to avoid the unnecessary widespread use of antibiotic compounds. There is thus a clinical need for macrolide compounds with clinically useful immunomodulatory activity but sufficiently low antimicrobial activity not to constitute a resistance-promotion hazard. Despite the significant interest in the development of such immunolides, suitable compounds have not yet been developed. Certain compounds are described in WO2014/166503 as having good non-antibiotic properties but reduced antimicrobial activity. In practice the compounds described therein do not have sufficient activity to be clinically useful.

Some limited numbers of derivatives of azithromycin are known, for example from patent publications WO2006/087644, WO2004/005310, WO2004/139821, WO03/070174 and CN1837225.

SUMMARY OF THE INVENTION

In a first embodiment, the invention provides a compound according to formula (I)

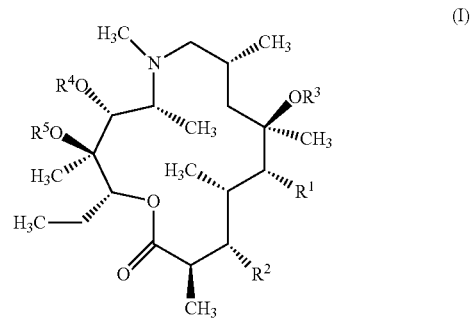

(I)

wherein
$R^1$ is selected from the group consisting of OH, carbamoyloxy, N—$C_{1-6}$-alkylcarbamoyloxy, N—($C_{6-14}$-aryl-$C_{1-6}$-alkyl)carbamoyloxy, N,N-di-$C_{1-6}$-alkylcarbamoyloxy, N,N-di-alkylcarbamoyloxy with the two alkyl substituents together forming a 5- to 8-membered heterocycle together with the nitrogen atom of the carbamate moiety, $C_{1-6}$-alkylcarboxy and a moiety according to formula (II)

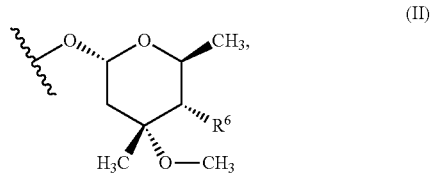

(II)

wherein
R$^6$ is selected from the group consisting of H, OH and C$_{1-6}$-alkyl, whereby alkyl, aryl and/or the heterocycle in R$^1$ is optionally substituted by 1 to 6 halogen and/or CN; and
R$^2$ is according to formula (III)

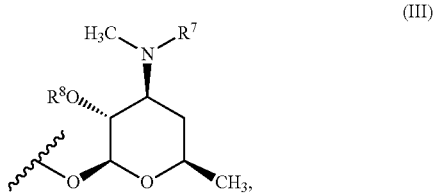

(III)

wherein
R$^7$ is selected from the group consisting of C$_{1-6}$-alkyl, C$_{6-14}$-aryl-C$_{1-6}$-alkyl, C$_{3-6}$-alkylcarbonyl, C$_{6-14}$-aryl-carbonyl, C$_{1-6}$-alkyl-C$_{6-14}$-arylcarbonyl, C$_{6-14}$-arylsulfonyl, C$_{1-6}$-alkyl-C$_{6-14}$-arylsulfonyl, C$_{6-14}$-aryl-C$_{1-6}$-alkylcarbonyl, C$_{6-14}$-aryl-O—C$_{1-6}$-alkylcarbonyl, C$_{6-14}$-aryl-C$_{1-6}$-alkyl-O—C$_{1-6}$-alkyl-carbonyl, HOOC—(CH$_2$)$_m$—(CO)— with
m being from 0 to 6,
a substituent of formula (V. 1)

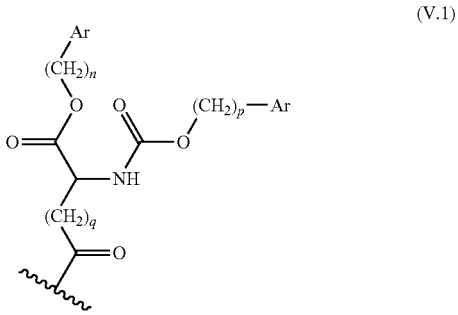

(V.1)

with Ar being C$_{6-14}$-aryl and n, p and q being independently from 0 to 6, C$_{6-14}$-aryl-C$_{1-6}$-alkyl-O—CO—NH—C$_{1-6}$-alkyl-CO—, and
C$_{6-14}$-arylsulfonyl, and C$_{1-6}$-alkyl-C$_{6-14}$-arylsulfonyl, whereby alkyl and/or aryl in R$^7$ is optionally substituted by 1 to 6 halogen and/or CN; and
R$^8$ is selected from the group consisting of H; C$_{6-14}$-arylcarbonyl optionally substituted with 1 to 5 groups selected from halogen atoms, C$_{1-3}$-alkyl sulfonyl groups, C$_{1-3}$-alkyl groups and/or C$_{1-3}$-alkoxy groups; C$_{3-6}$-alkylcarbonyl; HOOC—(CH$_2$)$_m$—(CO)— with m being from 0 to 6, a substituent of formula (V. 1) as depicted hereinbefore with Ar being C$_{6-14}$-aryl and n, p and q being independently from 0 to 6; and heteroaryl carbonyl having a 5- to 10-membered ring containing 1, 2 or 3 heteroatoms selected from the group consisting of O, N and S, the ring of the heteroaryl carbonyl optionally being substituted by 1 to 3 substituents selected from the group consisting of C$_{1-4}$-alkyl, C$_{1-4}$-alkoxy, C$_{2-4}$-alkenyl, C$_{2-4}$-alkenoxy, halogen and CN, whereby alkyl and/or aryl in R$^8$ is optionally substituted by 1 to 6 halogen and/or CN;
R$^3$ is H; and
R$^4$ and R$^5$ are independently selected from H and C$_{1-6}$-alkylcarbonyl, whereby alkyl is optionally substituted by 1 to 6 halogen and/or CN, or R$^4$ and R$^5$ together form a single carbonyl group which forms a cyclic carbonate with both oxygen atoms it is bonded to; and
provided that if R$^6$ is H or methyl, then R$^8$ is not H, and
provided that if R$^1$ is OH and R$^7$ is methyl, then R$^8$ is not H; and
provided that if R$^8$ is C$_4$ alkyl carbonyl, then R$^1$ is not a moiety according to formula (II);
or a pharmaceutically acceptable ester, amide, carbamate, solvate or salt thereof, including a salt of such an ester, amide or carbamate, and a solvate of such an ester, amide, carbamate or salt.

The invention further provides a pharmaceutical composition comprising at least one compound as defined above and at least one pharmaceutically acceptable excipient. In such a pharmaceutical composition, if R$^1$ is OH and R$^7$ is methyl, then R$^8$ can be H.

The invention further provides a compound or composition according to the invention for use as a medicament.

The invention further provides a compound or composition for use in the treatment of a disease or condition that is caused by a defect in epithelial cells or tissue, or a disease or condition that benefits from enhancement or restoration of epithelial barrier function.

The invention further provides a method for the treatment or prophylaxis of a disease or condition that is caused by a defect in epithelial cells or tissue, or a disease or condition that benefits from enhancement or restoration of epithelial barrier function, which comprises administering to the mammal a therapeutically effective amount of a compound or composition of the invention.

The compounds of the invention have been found by the current inventors to have good activity in a model of human airway epithelial regeneration, and to have reduced antimicrobial activity in a panel of tests against various bacteria. A compound of the invention has been tested in an in vivo model of barrier challenge in the lung and it has been found to provide a significant effect in the enhancement of lung epithelial barrier function.

The invention further provides compounds of formula (I) for use as a medicament.

DETAILED DESCRIPTION

As described above, the invention provides compounds of Formula (I). Preferred compounds of Formula (I) are the compounds according to the invention wherein R$^1$ is selected from the group consisting of OH, C$_{1-3}$-alkylcarboxy, a moiety according to formula (II)

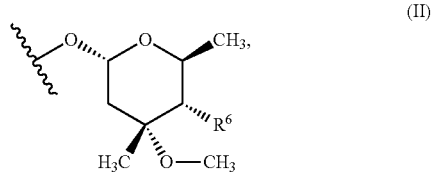

(II)

wherein R$^6$ is OH, and a moiety according to formula (IV)

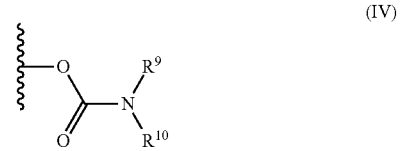

(IV)

wherein $R^9$ and $R^{10}$ are independently selected from the group consisting of H, $C_{1-3}$-alkyl and $C_{6-10}$-aryl-$C_{1-3}$-alkyl or are together alkyl forming a 5- or 6-membered aliphatic heterocycle together with the nitrogen atom they are both bonded to, whereby said heterocycle optionally contains one or two, preferably one further heteroatom(s) selected from the group consisting of N, O and S, preferably from the group consisting of N and O, more preferably optionally contains one or two further O atoms, yet more preferably optionally contains one further O atom, or said heterocycle is selected from the group consisting of piperidine, piperazine and morpholin, preferably is morpholin, whereby alkyl, aryl and/or the heterocycle in $R^1$ is optionally substituted by 1 to 6 halogen and/or CN.

Particularly preferred compounds according to the invention are those wherein $R^1$ is OH.

In Formula (I), $R^2$ is a group of formula (III)

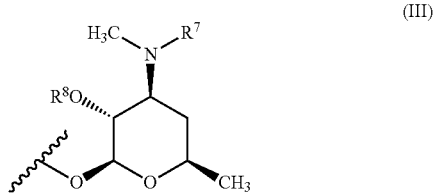

(III)

In an embodiment, $R^7$ is selected from the group consisting of $C_{1-6}$-alkyl, $C_{6-14}$-aryl-$C_{1-6}$-alkyl, $C_{6-14}$-arylcarbonyl, $C_{1-6}$-alkyl-$C_{6-14}$-arylcarbonyl, $C_{6-14}$-arylsulfonyl, $C_{1-6}$-alkyl-$C_{6-14}$-arylsulfonyl, $C_{6-14}$-aryl-$C_{1-6}$-alkylcarbonyl, $C_{6-14}$-aryl-O—$C_{1-6}$-alkylcarbonyl, $C_{6-14}$-aryl-$C_{1-6}$-alkyl-O—$C_{1-6}$-alkyl-carbonyl, HOOC—$(CH_2)_m$—(CO)— with m being from 0 to 6, a substituent of formula (V. 1)

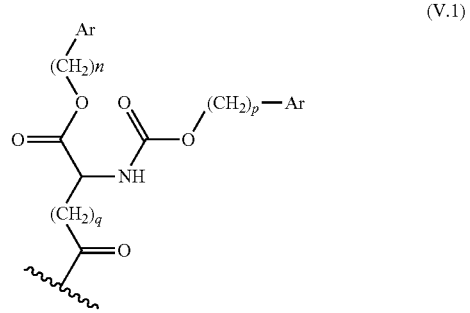

(V.1)

with Ar being $C_{6-14}$-aryl and n, p and q being independently from 0 to 6, $C_{6-14}$-aryl-$C_{1-6}$-alkyl-O—CO—NH—$C_{1-6}$-alkyl-CO—, and $C_{6-14}$-arylsulfonyl, and $C_{1-6}$-alkyl-$C_{6-14}$-arylsulfonyl, whereby alkyl and/or aryl in $R^7$ is optionally substituted by 1 to 6 halogen and/or CN More preferred compounds of the invention are those wherein $R^7$ is selected from the group consisting of $C_{1-3}$-alkyl, $C_{6-10}$-aryl-$C_{1-3}$-alkyl, linear or branched, preferably branched $C_{3-4}$-alkylcarbonyl, $C_{6-10}$-arylcarbonyl, $C_{6-10}$-aryl-$C_{1-3}$-alkylcarbonyl, $C_{6-10}$-aryl-O—$C_{1-3}$-alkylcarbonyl, $C_{6-10}$-aryl-$C_{1-3}$-alkyl-O—$C_{1-3}$-alkyl-carbonyl, HOOC—$(CH_2)_m$—(CO)— with m being from 0 to 3, preferably 1 to 3, most preferably 1 or 2, a moiety according to formula (V.2)

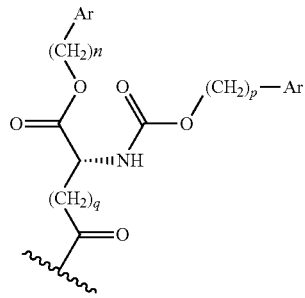

(V.2)

wherein Ar is $C_{6-10}$-aryl and n, p and q each are independently from 0 to 3, preferably n and p each are independently 1 or 2 and q is 2 or 3, most preferably n and p each are the same and 1 or 2 and q is 2 or 3, $C_{6-10}$-aryl-$C_{1-3}$-alkyl-O—CO—NH—$C_{1-3}$-alkyl-CO—, $C_{6-10}$-arylsulfonyl, and $C_{1-3}$-alkyl-$C_{6-10}$-arylsulfonyl.

Yet more preferably $R^7$ is selected from the group consisting of methyl, benzyl, benzoyl, naphthylsulfonyl, methylphenylsulfonyl, isopropyl carbonyl, succinyl, benzyl carbonyl, phenoxyethylcarbonyl, benzyloxymethylcarbonyl, benzyl-O—CO—NH—$CH_2$—CO— and a moiety according to formula (V.2) wherein Ar is phenyl, n=p=1 and q=2,
whereby alkyl and/or aryl in $R^7$ is optionally substituted by 1 to 6, preferably 1 to 3 halogen and/or CN.

In an embodiment, $R^8$ is selected from the group consisting of H; $C_{6-14}$-arylcarbonyl optionally substituted with 1 to 5 groups selected from halogen atoms, $C_{1-3}$-alkyl sulfonyl groups, $C_{1-3}$-alkyl groups and/or $C_{1-3}$-alkoxy groups; HOOC—$(CH_2)_m$—(CO)— with m being from 0 to 6, a substituent of formula (V. 1) as depicted hereinbefore with Ar being $C_{6-14}$-aryl and n, p and q being independently from 0 to 6; and heteroaryl carbonyl having a 5- to 10-membered ring containing 1, 2 or 3 heteroatoms selected from the group consisting of O, N and S, the ring of the heteroaryl carbonyl optionally being substituted by 1 to 3 substituents selected from the group consisting of $C_{1-4}$-alkyl, $C_{1-4}$-alkoxy, $C_{2-4}$-alkenyl, $C_{2-4}$-alkenoxy, halogen and CN,
whereby alkyl and/or aryl in $R^8$ is optionally substituted by 1 to 6 halogen and/or CN;

Preferably $R^8$ is selected from the group consisting of H, $C_{6-10}$-arylcarbonyl, $C_{6-10}$-arylcarbonyl substituted with 1 to 3 halogen atoms, $C_{1-2}$-alkyl groups and/or $C_{1-2}$-alkoxy groups, linear or branched, preferably branched $C_{3-4}$-alkylcarbonyl, HOOC—$(CH_2)_m$—(CO)— with m being from 0 to 3, preferably 1 to 3, most preferably 1 or 2, a moiety according to formula (V.2) as depicted hereinbefore wherein Ar is $C_{6-10}$-aryl and n, p and q each are independently from 0 to 3, preferably n and p each are independently 1 or 2 and q is 2 or 3, most preferably n and p each are the same and 1 or 2 and q is 2 or 3, $C_{1-3}$-alkylsulfonyl-bi-$C_{6-10}$-arylcarbonyl, and heteroaryl carbonyl having a 5-, 6- or 10-membered ring containing 1, 2 or 3 heteroatoms, more preferably 1 or 2 heteroatoms, most preferably 1 heteroatom, with the heteroatom(s) in each case being selected from the group consisting of N, O and S, preferably from the group consisting of N and O, most preferably being N, the ring of the heteroaryl carbonyl optionally being substituted by 1 or 2 substituents selected from the group consisting of $C_{1-2}$-alkyl, $C_{1-2}$-alkoxy, $C_{2-3}$-alkenyl, $C_{2-3}$-alkenoxy, halogen, in particular F and Cl, and CN, preferably selected from the group consisting of methyl, methoxy, F and Cl, most preferably selected from the group consisting of methyl and Cl.

Yet more preferably $R^8$ is selected from the group consisting of isopropyl carbonyl, succinyl, benzoyl, iodobenzoyl, ethylphenylcarbonyl, methoxyphenylcarbonyl, methylsulfonylphenylbenzoyl, naphthyl carbonyl, a moiety according to formula (V.2) wherein Ar is phenyl, n=p=1 and q=2, pyrazolylcarbonyl, dimethylpyrazolylcarbonyl, thiophenyl, chlorothiophenyl, pyridylcarbonyl and quinolylcarbonyl, whereby alkyl, aryl and/or the heterocycle in $R^8$ is optionally substituted by 1 to 6, preferably 1 to 3 halogen and/or CN.

For particularly preferred compounds of the invention $R^1$ is OH; and/or $R^7$ is selected from the group consisting of $C_{1-3}$-alkyl, in particular methyl, a moiety according to formula (V.2) wherein Ar is phenyl, n and p each are the same and 1 or 2 and q is 2 or 3, phenyl-$C_{1-2}$-alkyl-O—CO—NH—$C_{1-2}$-alkyl-CO— and phenyl-O—$C_{1-3}$-alkylcarbonyl, whereby alkyl, aryl and/or the heterocycle in $R^7$ is optionally substituted by 1 to 3 halogen and/or CN; and/or $R^8$ is selected from the group consisting of H, HOOC—$(CH_2)_m$—(CO)— with m being from 1 to 3, preferably 1 or 2, most preferably 2, benzoyl, methylbenzoyl, ethylbenzoyl, methoxybenzoyl, ethoxybenzoyl, methylsulfonylphenylbenzoyl and naphthylcarbonyl, whereby alkyl, aryl and/or the heterocycle in $R^8$ is optionally substituted by 1 to 3 halogen and/or CN.

For particularly preferred compounds of the invention $R^1$ is OH; $R^8$ is H and $R^7$ is selected from the group consisting of $C_{1-3}$-alkyl, in particular methyl, a moiety according to formula (V.2) wherein Ar is phenyl, n and p each are the same and 1 or 2 and q is 2 or 3, phenyl-$C_{1-2}$-alkyl-O—CO—NH—$C_{1-2}$-alkyl-CO— and phenyl-O—$C_{1-3}$-alkylcarbonyl, whereby alkyl, aryl and/or the heterocycle in $R^7$ is optionally substituted by 1 to 3 halogen and/or CN. Preferably, the $R^7$ group contains at least one aromatic ring.

For particularly preferred compounds of the invention $R^1$ is OH; $R^7$ is Me and $R^8$ is selected from the group consisting of H, HOOC—$(CH_2)_m$—(CO)— with m being from 1 to 3, preferably 1 or 2, most preferably 2, benzoyl, methylbenzoyl, ethylbenzoyl, methoxybenzoyl, ethoxybenzoyl, methylsulfonylphenylbenzoyl and naphthyl carbonyl, whereby alkyl and/or aryl in $R^8$ is optionally substituted by 1 to 3 halogen and/or CN. Preferably, the $R^8$ group contains at least one aromatic ring.

A particularly preferred group of compounds of the invention is the group in which $R^1$ is OH; $R^8$ is H and $R^7$ is selected from the group consisting of $C_{6-10}$-aryl-$C_{1-3}$-alkyl, $C_{6-10}$-arylcarbonyl, $C_{6-10}$-aryl-$C_{1-3}$-alkylcarbonyl, $C_{6-10}$-aryl-O—$C_{1-3}$-alkylcarbonyl, $C_{6-10}$-aryl-$C_{1-3}$-alkyl-O—$C_{1-3}$-alkyl-carbonyl, HOOC—$(CH_2)_m$—(CO)— with m being from 0 to 3, preferably 1 to 3, most preferably 1 or 2, a moiety according to formula (V.2) wherein Ar is $C_{6-10}$-aryl and n, p and q each are independently from 0 to 3, preferably n and p each are independently 1 or 2 and q is 2 or 3, most preferably n and p each are the same and 1 or 2 and q is 2 or 3, $C_{6-10}$-aryl-$C_{1-3}$-alkyl-O—CO—NH—$C_{1-3}$-alkyl-CO—, $C_{6-10}$-arylsulfonyl, and $C_{1-3}$-alkyl-$C_{6-10}$-arylsulfonyl; whereby alkyl and/or aryl in $R^7$ is optionally substituted by 1 to 6, preferably 1 to 3 halogen and/or CN groups.

A particularly preferred group of compounds of the invention is the group in which $R^1$ is OH; $R^8$ is H and $R^7$ is selected from the group consisting of benzyl, benzoyl, methylbenzoyl, ethylbenzoyl, methoxybenzoyl, ethoxybenzoyl, methylsulfonylphenylbenzoyl naphthyl carbonyl, naphthylsulfonyl, methylphenylsulfonyl, succinyl, and a moiety according to formula (V.2) wherein Ar is phenyl, n and p each are the same and 1 or 2 and q is 2 or 3. For $R^7$ benzyl, benzoyl, naphthylsulfonyl, methylphenylsulfonyl, succinyl, and a moiety according to formula (V.2) wherein Ar is phenyl, n and p each are the same and 1 or 2 and q is 2 or 3 are especially preferred.

An alternative particularly preferred compounds of the invention is the group in which $R^1$ is OH; $R^7$ is Me and $R^8$ is selected from the group consisting of $C_{6-10}$-arylcarbonyl, $C_{6-10}$-arylcarbonyl substituted with 1 to 3 halogen atoms, $C_{1-2}$-alkyl groups and/or $C_{1-2}$-alkoxy groups, branched $C_{3-4}$-alkylcarbonyl, HOOC—$(CH_2)_m$—(CO)— with m being from 0 to 3, preferably 1 to 3, most preferably 1 or 2, a moiety according to formula (V.2) as depicted hereinbefore wherein Ar is $C_{6-10}$-aryl and n, p and q each are independently from 0 to 3, preferably n and p each are independently 1 or 2 and q is 2 or 3, most preferably n and p each are the same and 1 or 2 and q is 2 or 3, $C_{1-3}$-alkylsulfonyl-bi-$C_{6-10}$-aryl-carbonyl, and heteroaryl carbonyl having a 5-, 6- or 10-membered ring containing 1, 2 or 3 heteroatoms, more preferably 1 or 2 heteroatoms, most preferably 1 heteroatom, with the heteroatom(s) in each case being selected from the group consisting of N, O and S, preferably from the group consisting of N and O, most preferably being N, the ring of the heteroarylcarbonyl optionally being substituted by 1 or 2 substituents selected from the group consisting of $C_{1-2}$-alkyl, $C_{1-2}$-alkoxy, $C_{2-3}$-alkenyl, $C_{2-3}$-alkenoxy, halogen, in particular F and Cl, and CN, preferably selected from the group consisting of methyl, methoxy, F and Cl, most preferably selected from the group consisting of methyl and Cl. Within the $R^8$ group, an alkyl, aryl and/or heterocyclic group may optionally be substituted by 1 to 6, preferably 1 to 3 halogen atoms and/or CN group(s).

A further particularly preferred compounds of the invention is the group in which $R^1$ is OH; $R^7$ is Me and $R^8$ is selected from the group consisting of isopropyl carbonyl, succinyl, benzoyl, halobenzoyl (for example iodobenzoyl), ethylphenylcarbonyl, methoxyphenylcarbonyl, methylsulfonylphenylbenzoyl, naphthyl carbonyl, a moiety according to formula (V.2) wherein Ar is phenyl, n=p=1 and q=2, pyrazolylcarbonyl, dimethylpyrazolylcarbonyl, thiophenyl, chlorothiophenyl, pyridylcarbonyl and quinolylcarbonyl.

A particularly preferred group of compounds of the invention are compounds of Formula (I) herein $R^1$ is OH;

$R^2$ is according to formula (III)

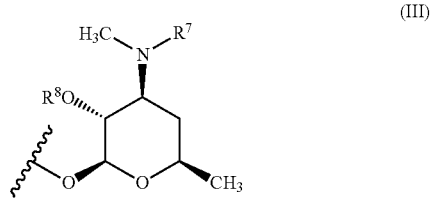

(III)

wherein $R^7$ is $C_{1-6}$-alkyl; and $R^8$ is selected from the group consisting of $C_{6-14}$-arylcarbonyl optionally substituted with 1 to 5 groups selected from $C_{1-3}$-alkyl sulfonyl groups and/or $C_{1-3}$-alkyl groups; HOOC—$(CH_2)_m$—(CO)— with m being from 0 to 6, a substituent of formula (V.1)

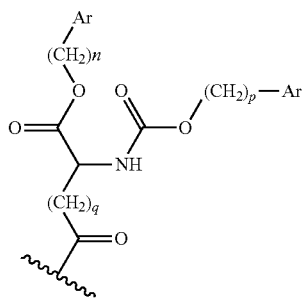

(V.1)

with Ar being $C_{6-14}$-aryl and n, p and q being independently from 0 to 6;

$R^3$ is H; and $R^4$ and $R^5$ are both H;

or a pharmaceutically acceptable ester, amide, carbamate, solvate or salt thereof, including a salt of such an ester, amide or carbamate, and a solvate of such an ester, amide, carbamate or salt.

In such a compound, for example $R^7$ is Me. For example, $R^7$ is Me and $R^8$ is selected from the group consisting of $C_{6-10}$-arylcarbonyl, $C_{6-10}$-arylcarbonyl substituted with 1 to 3 $C_{1-2}$-alkyl sulfonyl groups or $C_{1-2}$-alkyl groups, HOOC—$(CH_2)_m$—(CO)— with m being from 0 to 3, preferably 1 to 3, most preferably 1 or 2, a moiety according to formula (V.1) as depicted hereinbefore wherein Ar is $C_{6-10}$-aryl and n, p and q each are independently from 0 to 3, preferably n and p each are independently 1 or 2 and q is 2 or 3, most preferably n and p each are the same and 1 or 2 and q is 2 or 3. Within the $R^8$ group, an alkyl, aryl and/or heterocyclic group may optionally be substituted by 1 to 6, for example 1 to 3 halogen atoms and/or CN group(s). For example, $R^7$ is Me and $R^8$ is selected from the group consisting of succinyl, benzoyl, halobenzoyl (for example iodobenzoyl), ethylphenylcarbonyl, methylsulfonylphenylbenzoyl, naphthylcarbonyl and a moiety according to formula (V.2) wherein Ar is phenyl, n=p=1 and q=2.

Further preferred compounds according to the invention are the following:

(2R,3S,4R,5R,8R,10S,11R,12S,13S,14R)-11-{[(2S,3R,4S,6R)-4-(dimethylamino)-3-hydroxy-6-methyloxan-2-yl]oxy}-2-ethyl-3,4,10,13-tetrahydroxy-3,5,6,8,10,12,14-heptamethyl-1-oxa-6-azacyclopentadecan-15-one (Example 1);

(2S,3R,4S,6R)-4-(dimethylamino)-2-{[(2R,3S,4R,5R,8R,10S,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl benzoate (Example 2);

(3aR,4R,7R,8S,9S,10R,11S,13R,16R,16aR)-10-{[(2S,3R,4S,6R)-3-(benzoyloxy)-4-(dimethylamino)-6-methyloxan-2-yl]oxy}-4-ethyl-li-hydroxy-3a,7,9,11,13,15,16-heptamethyl-2,6-dioxo-tetradecahydro-2H-[1,3]dioxolo[4,5-c]1-oxa-6-azacyclopentadecan-8-yl morpholine-4-carboxylate (Example 3);

(2S,3R,4S,6R)-2-{[(3aR,4R,7R,8S,9S,10R,11S,13R,16R,16aR)-8-[(benzylcarbamoyl)oxy]-4-ethyl-11-hydroxy-3a,7,9,11,13,15,16-heptamethyl-2,6-dioxo-tetradecahydro-2H-[1,3]dioxolo[4,5-c]1-oxa-6-azacyclopentadecan-10-yl]oxy}-4-(dimethylamino)-6-methyloxan-3-yl benzoate (Example 4);

(2R,3S,4R,5R,8R,10S,11R,12S,13S,14R)-11-{[(2S,3R,4S,6R)-4-[benzyl(methyl)amino]-3-hydroxy-6-methyloxan-2-yl]oxy}-2-ethyl-3,4,10-trihydroxy-13-{[(4R,5S,6S)-5-hydroxy-4-methoxy-4,6-dimethyloxan-2-yl]oxy}-3,5,6,8,10,12,14-heptamethyl-1-oxa-6-azacyclopentadecan-15-one (Example 5);

N-[(2S,3R,4S,6R)-2-{[(2R,3S,4R,5R,8R,10S,11R,12S,13S,14R)-2-ethyl-3,4,10-trihydroxy-13-{[(4R,5S,6S)-5-hydroxy-4-methoxy-4,6-dimethyloxan-2-yl]oxy}-3,5,6,8,10,12,14-heptamethyl-15-oxo-1-oxa-6-azacyclopentadecan-11-yl]oxy}-3-hydroxy-6-methyloxan-4-yl]-N-methylbenzamide (Example 6);

N-[(2S,3R,4S,6R)-2-{[{2R,3S,4R,5R,8R,10S,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-3-hydroxy-6-methyloxan-4-yl]-N-methylbenzamide (Example 7);

N-[(2S,3R,4S,6R)-2-{[(2R,3 S,4R,5R,8R,10S,11R,12S,13 S,14R)-2-ethyl-3,4,10-trihydroxy-13-{[(4R,5S,6S)-5-hydroxy-4-methoxy-4,6-dimethyloxan-2-yl]oxy}-3,5,6,8,10,12,14-heptamethyl-15-oxo-1-oxa-6-azacyclopentadecan-11-yl]oxy}-3-hydroxy-6-methyloxan-4-yl]-N-methylnaphthalene-2-sulfonamide (Example 8);

N-[(2S,3R,4S,6R)-2-{[(2R,3 S,4R,5R,8R,10S,11R,12S,13 S,14R)-2-ethyl-3,4,10,13-tetrahydroxy-3,5,6,8,10,12,14-heptamethyl-15-oxo-1-oxa-6-azacyclopentadecan-11-yl]oxy}-3-hydroxy-6-methyloxan-4-yl]-N-methylnaphthalene-2-sulfonamide (Example 9);

N-[(2S,3R,4S,6R)-2-{[(2R,3 S,4R,5R,8R,10S,11R,12S,13 S,14R)-2-ethyl-3,4,10-trihydroxy-13-{[(4R,5S,6S)-5-hydroxy-4-methoxy-4,6-dimethyloxan-2-yl]oxy}-3,5,6,8,10,12,14-heptamethyl-15-oxo-1-oxa-6-azacyclopentadecan-11-yl]oxy}-3-hydroxy-6-methyloxan-4-yl]-N,4-dimethylbenzene-1-sulfonamide (Example 10);

(2S,3R,4S,6R)-2-{[(2R,3R,4R,5R,8R,10S,11R,12S,13S,14R)-4,13-bis(acetyloxy)-2-ethyl-3,10-dihydroxy-3,5,6,8,10,12,14-heptamethyl-15-oxo-1-oxa-6-azacyclopentadecan-11-yl]oxy}-4-(dimethylamino)-6-methyloxan-3-yl benzoate (Example 11);

(2S,3R,4S,6R)-4-(dimethylamino)-2-{[(2R,3 S,4R,5R,8R,10S,11R,12S,13 S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl 4-(4-methanesulfonylphenyl)benzoate (Example 12);

(2S,3R,4S,6R)-2-{[(2R,3 S,4R,5R,8R,10S,11R,12S,13 S,14R)-2-ethyl-3,4,10,13-tetrahydroxy-3,5,6,8,10,12,14-heptamethyl-15-oxo-1-oxa-6-azacyclopentadecan-11-yl]oxy}-6-methyl-4-(N-methylnaphthalene-2-sulfonamido)oxan-3-yl benzoate (Example 13);

{2S,3R,4S,6R)-4-(dimethylamino)-2-{[(2R,3S,4R,5R,8R,10S,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl 4-iodobenzoate (Example 14);

1-benzyl (2S,3R,4S,6R)-4-(dimethylamino)-2-{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl (2R)-2-{[(benzyloxy)carbonyl]amino}pentanedioate (Example 15);

benzyl (2R)-2-{[(benzyloxy)carbonyl]amino}-4-{[(2S,3R,4S,6R)-2{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-3-hydroxy-6-methyloxan-4-yl](methyl)carbamoyl} butanoate (Example 16);

4-{[(2S,3R,4S,6R)-4-(dimethylamino)-2-{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6- azacyclopentadecan-11-yl]oxy}-6-methyloxan-3-yl]oxy}-4-oxobutanoic acid (Example 17);

3-{[(2S,3R,4S,6R)-2-{[(2R,3S,4R,5R,8R,10R,11S,13S,14R)-2-ethyl-3,4,10,13-tetrahydroxy-3,5,6,8,10,12,14-heptamethyl-15-oxo-1-oxa-6-azacyclopentadecan-11-yl]oxy}-3-hydroxy-6-methyloxan-4-yl](methyl)carbamoyl}propanoic acid (Example 18); and (2S,3R,4S,6R)-4-(dimethylamino)-2-{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl pyridine-3-carboxylate (Example 19);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl]2,5-dimethylpyrazole-3-carboxylate (Example 20);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 5-chlorothiophene-2-carboxylate (Example 21);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-ethylbenzoate (Example 22);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-methoxybenzoate (Example 23);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] naphthalene-2-carboxylate (Example 24);

[(2S,3R,4S,6R)-4-(dimethylamino)-2-[[(2R,3 S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] quinoline-3-carboxylate (Example 25);

2-benzyloxy-N-[(2S,3R,4S,6R)-2-[[(2R,3 S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-acetamide (Example 26);

benzyl N-[2-[[(2S,3R,4S,6R)-2-[[(2R,3 S,4R,5R,8R,10R,11R,12S,13 S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-methyl-amino]-2-oxo-ethyl]carbamate (Example 27);

N-[(2S,3R,4S,6R)-2-[[(2R,3 S,4R,5R,8R,10R,11R,12S,13 S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-3-phenoxy-propanamide (Example 28);

N-[(2S,3R,4S,6R)-2-[[(2R,3 S,4R,5R,8R,10R,11R,12S,13 S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-2-phenyl-acetamide (Example 29);

(2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Example 30);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 2-methylpropanoate (Example 31);

most preferably selected from the group consisting of (2S,3R,4S,6R)-4-(dimethylamino)-2-{[(2R,3S,4R,5R,8R,10S,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl benzoate (Example 2);

(2S,3R,4S,6R)-4-(dimethylamino)-2-{[(2R,3S,4R,5R,8R,10S,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl 4-(4-methanesulfonylphenyl)benzoate (Example 12);

1-benzyl (2S,3R,4S,6R)-4-(dimethylamino)-2-{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl (2R)-2-{[(benzyloxy)carbonyl]amino}pentanedioate (Example 15);

benzyl (2R)-2-{[(benzyloxy)carbonyl]amino}-4-{[(2S,3R,4S,6R)-2{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-3-hydroxy-6-methyloxan-4-yl](methyl)carbamoyl} butanoate (Example 16);

4-{[(2S,3R,4S,6R)-4-(dimethylamino)-2-{[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadecan-11-yl]oxy}-6-methyloxan-3-yl]oxy}-4-oxobutanoic acid (Example 17);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-ethylbenzoate (Example 22);

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] naphthalene-2-carboxylate (Example 24);

benzyl N-[2-[[(2S,3R,4S,6R)-2-[[(2R,3 S,4R,5R,8R,10R,11R,12S,13 S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-methyl-amino]-2-oxo-ethyl]carbamate (Example 27); and N-[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-3-phenoxy-propanamide (Example 28).

The invention also provides a pharmaceutical composition comprising at least one compound of the invention and at least one pharmaceutically acceptable excipient, whereby this also includes compounds for which $R^8$ can be H if $R^1$ is OH and $R^7$.

The compounds or compositions of the invention are suitable for use as medicaments, whereby this also includes compounds for which $R^8$ can be H if $R^1$ is OH and $R^7$.

As mentioned above, the compounds of the invention have been found by the current inventors to have good activity in a model of human airway epithelial regeneration, and to have reduced antimicrobial activity in a panel of tests against various bacteria. There are various in vitro and in vivo tests of epithelial barrier function that can be used to evaluate compounds of the invention. In vivo tests include challenge with the pathogenic agent $SO_2$, challenge with rhamnolipids, and challenge with hyperbaric trauma. A compound of the invention has been tested in vivo in an $SO_2$ challenge experiment and the compound was found to provide a significant effect in protecting lung epithelial barrier function.

The compounds or pharmaceutical compositions according to the invention are effective in the treatment of a disease or condition that is caused by a defect in epithelial cells or tissue, or a disease or condition that benefits from enhancement or restoration of epithelial barrier function. The disease or condition can be an airways disease and the epithelial tissue can be in the respiratory tract epithelial tissue, particularly a part of the respiratory tract selected from the group consisting of nose, nasal cavity, sinuses, larynx, trachea, bronchi, bronchioles, terminal airways and alveoli.

The compounds or compositions according to the invention are effective in the treatment of inborn, chronic, persistent or prolonged airway diseases. For example, they are effective in the treatment of conditions including asthma, chronic obstructive pulmonary disease (COPD), Cystic Fibrosis (CF), non-CF Bronchiectasis, chronic rhinosinusitis, diffuse panbronchiolitis (DPB), chronic bronchitis, Bronchiolitis Obliterans Organizing Pneumonia (BOOP) primary or secondary to chemotherapy or post-transplantation status, infantile respiratory distress syndrome (IRDS) and its long term complication, bronchopulmonary dysplasia, neuromuscular respiratory depression and/or failure, pneumonia (particularly community-acquired pneumonia) and conditions caused by and associated with Respiratory Syncytial Virus (RSV) and related viruses, for example the Human-Meta-Pneumo Virus, such as chronic infantile wheezing and associated childhood asthma bronchial hyperreactivity.

The compound or composition according to the invention is also effective in enhancement or restoration of epithelial barrier function in many diseases and disorders commonly associated with inflammation, said diseases preferably being selected from the group consisting of systemic inflammatory distress syndrome (SIRS), adult respiratory distress syndrome (ARDS), inflammatory bowel disease, ulcerative colitis and Crohn's disease.

The invention also provides a method for the treatment or prophylaxis of any disease or condition as mentioned herein, which comprises administering to the subject (for example a mammal, typically a human) a therapeutically effective amount of a compound or composition according to the invention.

Depending upon the substituents present in compounds of the formula (I), the compounds may form esters, amides, carbamates and/or salts. Salts and solvates of compounds of formula (I) which are suitable for use in medicine are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable esters, amides or carbamates salts, or solvates thereof.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Compounds of formula (I) may have an appropriate group converted to an ester, an amide or a carbamate. Thus typical ester and amide groups formed from an acid group in the compound of formula (I) include —$COOR^B$, —$CONR^B{}_2$, —$SO_2.OR^B$, or —$SO_2.NR^B{}_2$, while typical ester and amide and carbamate groups formed from an —OH or —$NR^B$ group in the compound of formula (I) include —$O.CO.R^B$, —$NR^B.CO.R^B$—$NR^B.CO_2R^B$—$O.SO_2R^B$, and —$NR^B.SO_2R^B$, wherein each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, $C_{6-10}$aryl and $C_{6-10}$ aryl$C_{1-6}$alkyl, each optionally substituted by from 1 to 3 halogen atoms. Preferably, each $R^B$ is independently selected from the group consisting of hydrogen and $C_{1-4}$alkyl. For example, in compounds of formula (I), one or more of the OH groups that are present when one or more of $R^3$, $R^4$ and $R^5$ are H can be converted to an ester of formula —$O.CO.R^B$; that is to say that the compound would have one or more of $R^3$, $R^4$ and $R^5$ represented by $CO.R^B$, $R^B$ being as given immediately above.

A compound which, upon administration to the recipient, is capable of being converted into a compound of formula (I) as described above, or an active metabolite or residue thereof, is known as a "prodrug". A prodrug may, for example, be converted within the body, e. g. by hydrolysis in the blood, into its active form that has medical effects. Certain esters, amides and carbamates described above can be prodrugs. Pharmaceutically acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl and 2-propenyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl 1-propynyl and 2-propynyl.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo [2. 2.1]hept-2-yl. Preferably, the cycloalkyl group is monocyclic.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aromatic group, one of the rings may, for example, be partially saturated. Examples of such groups include indanyl and tetrahydronaphthyl. Specifically, the term $C_{5-10}$ aryl is used herein to mean a group comprising from 5 to 10 carbon atoms in a monocyclic or bicyclic aromatic group. A particularly preferred $C_{5-10}$ aryl group is phenyl.

As used herein, the term "halogen" means fluorine, chlorine, bromine or iodine. Fluorine, chlorine and bromine are particularly preferred.

As used herein, the term "heterocyclyl" means an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. In a bicyclic heterocyclyl group there may be one or more heteroatoms in each ring, or only in one of the rings. A heteroatom is preferably O or N. Heterocyclyl groups containing a suitable nitrogen atom include the corresponding N-oxides.

Examples of monocyclic non-aromatic heterocyclyl groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

Examples of preferred heterocyclyl groups include piperidinyl, tetrahydrofuranyl, tetrahydropyranyl, pyridyl, pyrimidinyl and indolyl. Preferred heterocyclyl groups also include thienyl, thiazolyl, furanyl, pyrazolyl, pyrrolyl, isoxazolyl and imidazolyl.

As used herein the term "cycloalkylalkyl" means a group cycloalkyl-alkyl-attached through the alkyl group, "cycloalkyl" and "alkyl" being understood to have the meanings outlined above.

The compounds of the invention contain several chiral (asymmetric) centers and the molecules as a whole are chiral. The individual stereoisomers (enantiomers and diastereoisomers) and mixtures of these are within the scope of the present invention.

The compounds of the invention can be prepared by methods well known in the art. Azythromycin is widely available from commercial sources, including Sigma-Aldrich. The key intermediate Descladinose Azithromycin (Example 1) can be prepared by selective acidic hydrolysis of Azythromycin using methanol HCl(aq), following a published protocol as shown in Scheme 1. The key intermediates demethylated Azithromycin (Intermediate A), and demethylated Descladinose Azithromycin (Intermediate B) can be prepared by N-demethylation using iodine and NaOAc in MeOH or iPrOH, which method is set out in U.S. Pat. No. 3,725,385 and also described in European Journal of Medicinal Chemistry 49 (2012) 365-378, entry 5.1.3. That is also shown in Scheme 1:

Scheme 1

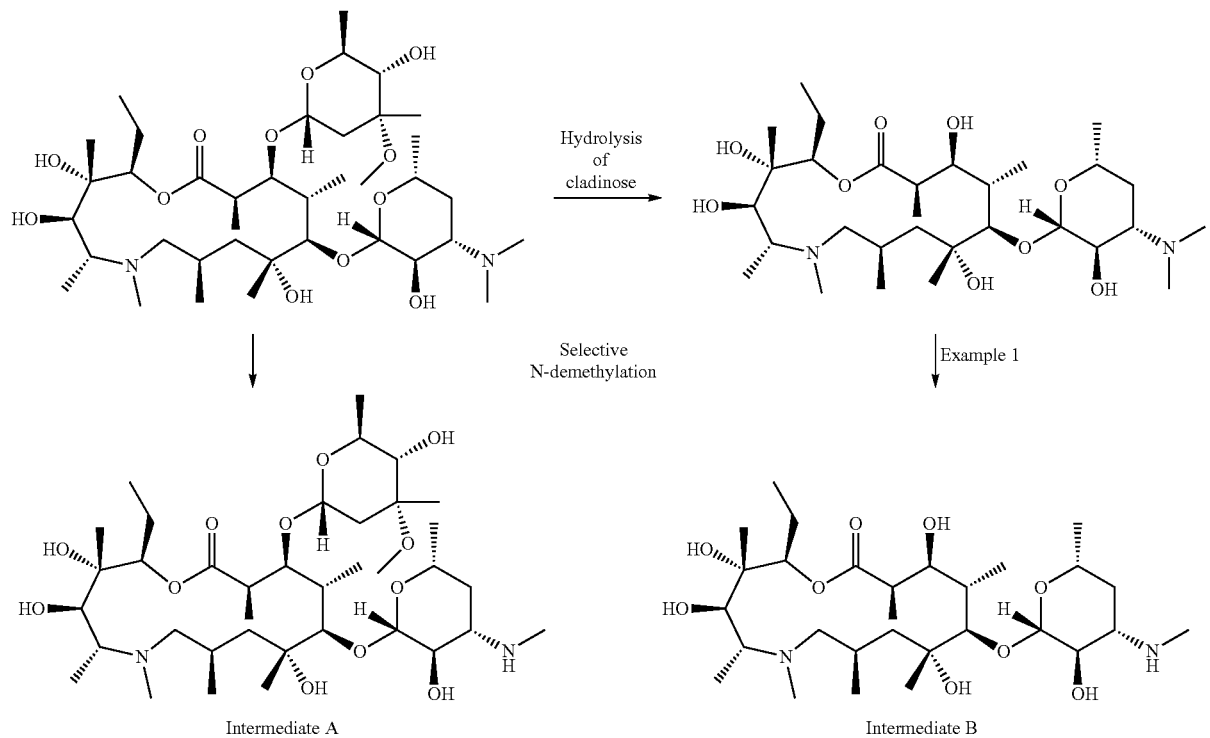

Intermediate A

Intermediate B

The advanced intermediates shown in Scheme 1 can be derivatised to compounds of the invention using standard coupling techniques.

The compounds of the invention are useful as medicaments. In particular, they are useful as medicaments for the treatment of a disease or condition that is caused by a defect in epithelial cells or tissue, or a disease or condition that benefits from enhancement or restoration of epithelial barrier function. The disease or condition can be an airways disease and the epithelial tissue can be in the respiratory tract epithelial tissue, particularly a part of the respiratory tract selected from the group consisting of, nose, nasal cavity, sinuses, larynx, trachea, bronchi, bronchioles, terminal airways and alveoli.

The compounds or compositions according to the invention are useful as medicaments for the treatment of inborn, chronic, persistent or prolonged airway diseases. For example, they are effective in the treatment of conditions including asthma, chronic obstructive pulmonary disease (COPD), Cystic Fibrosis (CF), non-CF Bronchiectasis, chronic rhinosinusitis, diffuse panbronchiolitis (DPB), chronic bronchitis, Bronchiolitis Obliterans Organizing Pneumonia (BOOP) primary or secondary to chemotherapy or post-transplantation status, infantile respiratory distress syndrome (IRDS) and its long term complication, bronchopulmonary dysplasia, neuromuscular respiratory depression and/or failure, pneumonia (particularly community-acquired pneumonia) and conditions caused by and associated with Respiratory Syncytial Virus (RSV) and related viruses, for example the Human-Meta-Pneumo Virus, such as chronic infantile wheezing and associated childhood asthma bronchial hyperreactivity.

The compounds of the invention are useful as medicaments for the treatment or prophylaxis of diseases and disorders commonly associated with inflammation that benefit from enhancement or restoration of epithelial barrier function, said diseases preferably being selected from the group consisting of systemic inflammatory distress syndrome (STRS), adult respiratory distress syndrome (ARDS), inflammatory bowel disease, ulcerative colitis and Crohn's disease.

The invention also provides a method for the treatment or prophylaxis of a disease or condition that is caused by a defect in epithelial cells or tissue, or a disease or condition that benefits from enhancement or restoration of epithelial barrier function. Conditions and diseases that may be treated by the method of the invention are preferably those described above. The invention also provides a method for the treatment or prophylaxis of conditions associated with inflammation that benefit from enhancement or restoration of epithelial barrier function. Such conditions and diseases are preferably those described above.

The invention also provides the use of a compound according to the invention, for the manufacture of a medicament for the treatment or prophylaxis of a disease or condition that is caused by a defect in epithelial cells or tissue, or a disease or condition that benefits from enhancement or restoration of epithelial barrier function. Conditions and diseases that may be treated are preferably those described above. The invention also provides the use of a compound according to the invention, for the manufacture of a medicament for the treatment or prophylaxis of conditions associated with inflammation that benefit from enhancement or restoration of epithelial barrier function. Such conditions and diseases are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Certain compounds of the invention have better oral bioavailability than others. A compound with particularly good bioavailability (particularly oral bioavailability) is especially useful in the treatment of conditions that are suited to treatment by systemic drug delivery. A compound with poorer bioavailability, on the other hand, lends itself to topical delivery (and systemic side effects will be minimized by the low bioavailability) and thus to the treatment of conditions that are suited to treatment by topical drug delivery (for example by inhalation or by dermal, buccal, sublingual or intraocular application.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. The typical daily dose is thus from about 1 mg to about 500 mg of the active ingredient, preferably from about 20 mg to about 500 mg of active ingredient, for example 50 mg to 500 mg, for example 100 mg to 400 mg, for example 200 mg to 300 mg, for example 250 mg of the active ingredient. For oral administration, the compositions are preferably provided in the form of tablets or other forms of presentation provided in discrete units containing 0.1, 0.5, 1.0, 2.5, 5.0, 10.0, 15.0, 25.0, 50.0, 100, 200, 250 or 500 milligrams of the active ingredient for the symptomatic adjustment of the dosage to the patient to be treated.

Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous (bolus or infusion), and intraarticular), inhalation (including fine particle dusts or mists which may be generated by means of various types of metered dose pressurized aerosols, nebulizers or insufflators), rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further active agents. Such further active agents may be further compounds according to the invention, or they may be different therapeutic agents, for example a further compound useful in the treatment of a respiratory condition or disease, for example a compound useful in the treatment of asthma, chronic obstructive pulmonary disease (COPD) or Cystic Fibrosis (CF).

Compounds useful in the treatment of asthma include Inhaled corticosteroids (for example fluticasone (Flonase, Flovent HFA), budesonide (Pulmicort Flexhaler, Rhinocort), flunisolide (Aerospan HFA), ciclesonide (Alvesco, Omnaris, Zetonna), beclomethasone (Qnasl, Qvar), mometasone (Asmanex) or fluticasone furoate (Arnuity Ellipta)), Leukotriene modifiers (for example montelukast (Singulair), zafirlukast (Accolate) or zileuton (Zyflo); Long-acting beta agonists (for example salmeterol (Serevent) or formoterol (Foradil, Perforomist); Combination inhalers (for example fluticasone-salmeterol (Advair Diskus/Seretide), budesonide-formoterol (Symbicort) or formoterol-mometasone (Dulera) containing a long-acting beta agonist along with a corticosteroid); Theophylline (for example Theo-24 or Elixophyllin), Short-acting beta agonists (for example albuterol (ProAir HFA, Ventolin HFA, others) and levalbuterol (Xopenex)), Ipratropium (Atrovent) or oral or intravenous corticosteroids (for example prednisone or methylprednisolone)

Compounds useful in the treatment of COPD include short-acting bronchodilators (for example albuterol (ProAir HFA, Ventolin HFA, others), levalbuterol (Xopenex), and ipratropium (Atrovent)), long-acting bronchodilators (including tiotropium (Spiriva), salmeterol (Serevent), formoterol (Foradil, Perforomist), arformoterol (Brovana), indacaterol (Arcapta) and aclidinium (Tudorza)), Inhaled steroids (including Fluticasone (Flovent) and budesonide (Pulmicort), Combination inhalers (for example combining bronchodilators and inhaled steroids, for example Salmeterol and fluticasone (Advair) and formoterol and budesonide (Symbicort)), Oral steroids, Phosphodiesterase-4 inhibitors (for example roflumilast (Daliresp)) Theophylline and Antibiotics.

Compounds useful in the treatment of CF include Antibiotics, Mucus-thinning drugs, Bronchodilators and Oral pancreatic enzymes.

If the compound of the invention is to be used for the treatment of a condition associated with inflammation that benefits from enhancement or restoration of epithelial barrier function, then the further active agent is selected from the agents suitable for the condition in question.

The above other therapeutic agents, when employed in combination with the compounds of the present invention, may be used, for example, in those amounts indicated in the Physicians' Desk Reference (PDR) or as otherwise determined by one of ordinary skill in the art.

The following Examples illustrate the invention.

EXAMPLES

General Methods

Preparative reversed phase chromatography was performed on X-bridge, prep C18 (5 μm), 50 mM ammonium bicarbonate/acetonitrile gradient. All compounds were analyzed by analytical HPLC/LCMS. The analysis was performed using an Agilent 1100 Series Liquid Chromatograph/Mass Selective Detector (MSD) (Single Quadrupole) equipped with an electrospray interface and a UV diode array detector. The compounds prepared were given IUPAC names obtained from the software Marvin Sketch 5.2.6.

Starting materials were obtained from conventional, ready-available sources.

For all of the compounds MS/ESI, positive ionization gives [M+H]⁺. The yield of the transformations are omitted due to that it more reflects the work of purification than the yield in the transformation to the desired product. The isolated yield of each of the compounds is in excess of the desired 50 mg with a few exceptions.

Example 1: Descladinose Azithromycin: (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one)

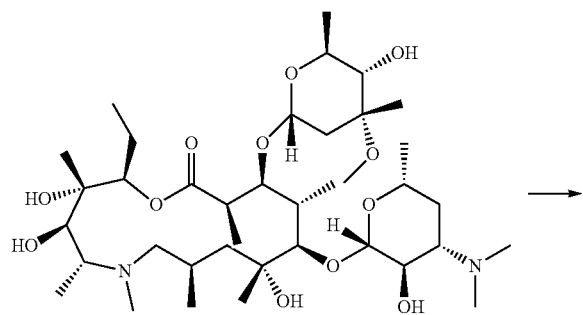

To a solution of Azythromycin ((2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-1-oxa-6-azacyclopentadecan-15-one) (10 g, 13.35 mmol) in Methanol (100 mL) HCl (1M) was added until pH was stabilized at 1.25 and the resulting solution was stirred for 24 h at room temperature. The mixture was again pH adjusted but using NaOH (1M) to pH 10.75. The mixture was stirred for 1 h and portioned between NaHCO₃ (5%) and DCM. The aqueous phase was washed with a second portion of DCM and the combined organic fractions were dried over magnesium sulphate and the solvent removed under reduced pressure giving the product as a white foam. A sample was purified by straight phase silica chromatography (DCM to 5% Methanol in DCM, 0.1% triethylamine added to the mobile phase)

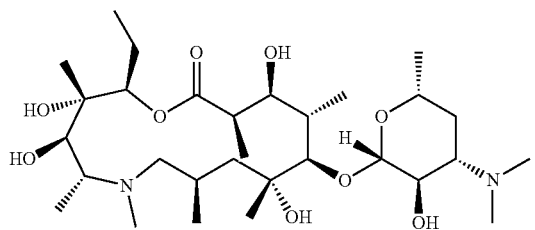

Example 2: (2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] benzoate)

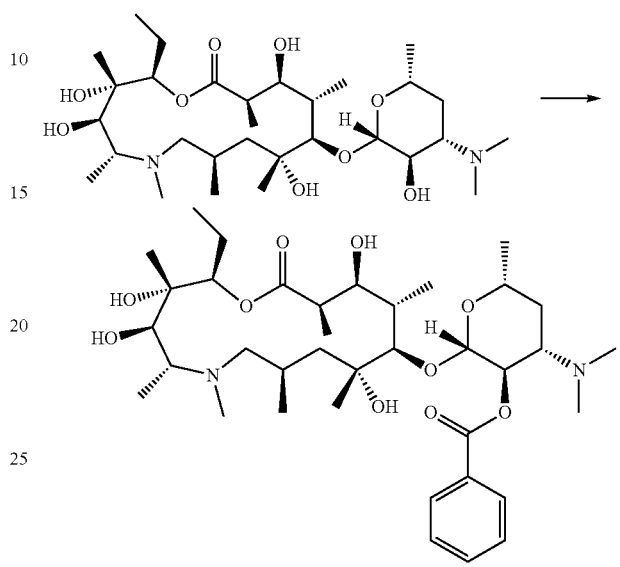

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (0.5 g, 0.8500 mmol) and Triethylamine (428.2 mg, 4.23 mmol) in DCM (5 ml), cooled on ice, was added Benzoyl chloride (356.9 mg, 2.54 mmol). The reaction mixture was allowed to reach room temperature. After 3 days good conversion to the desired benzoylated product was obtained and the mixture was portioned between DCM and saturated sodium hydrogen carbonate solution. The organic phase was dried over magnesium sulphate and concentrated to a white foam. The product was purified using reversed phase chromatography (see general information)

Example 3: (1R,2R,5R,7R,8R,9S,10S,11R,14R,15R)-8-[(2S,3R,4S,6R)-3-benzoyloxy-4-(dimethylamino)-6-methyl-tetrahydropyran-2-yl]oxy-14-ethyl-7-hydroxy-2,3,5,7,9,11,15-heptamethyl-12,17-dioxo-13,16,18-trioxa-3-azabicyclo[13.3.0]octadecan-10-yl]morpholine-4-carboxylate)

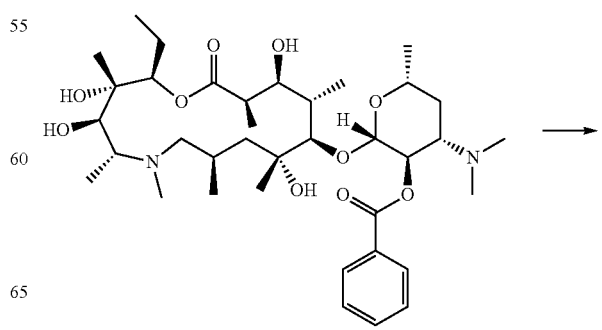

-continued

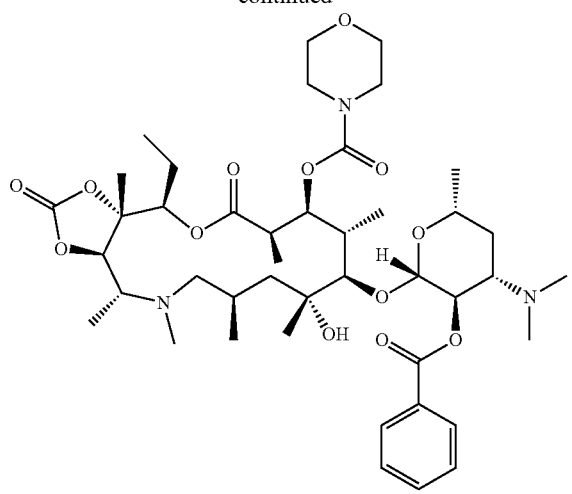 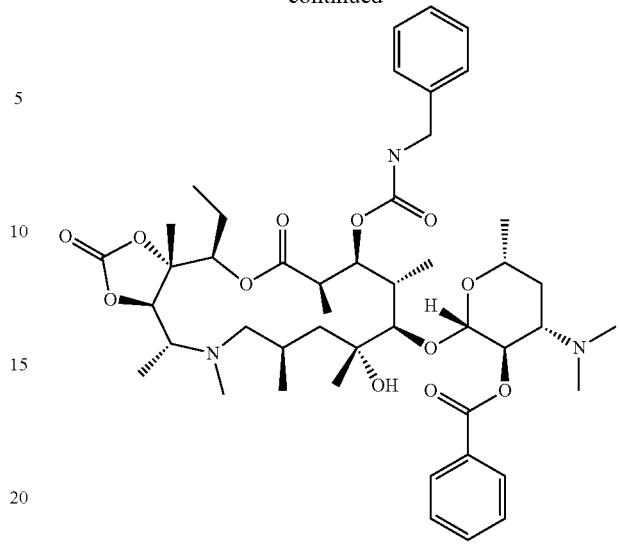

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] benzoate (Example 2) (250.mg, 0.3600 mmol) was mixed with Carbonyldiimidazole (466.73 mg, 2.88 mmol) and Triethylamine (291.27 mg, 2.88 mmol) in THE (2.5 mL). After stirring for 2 days the intermediate product was isolated by portioning between DCM and saturated sodium hydrogen carbonate solution. The DCM phase was dried over magnesium sulphate and concentrated under reduced pressure. DMF (1 mL) was added followed by Morpholine (37.61 mg, 0.4300 mmol) and 1,8-Diazabicyclo[5.4.0]undec-7-ene (65.73 mg, 0.4300 mmol). When no starting material was left the material was again portioned between DCM and saturated sodium hydrogen carbonate solution. The DCM phase was again dried over magnesium sulphate and concentrated under reduced pressure. The material was dissolved in acetonitrile and purified by reversed phase chromatography (see general methods). The clean fractions were concentrated and lyophilized to a solid.

Example 4: [(2S,3R,4S,6R)-2-[[(1R,2R,5R,7R,8R,9S,10S,11R,14R,15R)-10-(benzylcarbamoyloxy)-14-ethyl-7-hydroxy-2,3,5,7,9,11,15-heptamethyl-12,17-dioxo-13,16,18-trioxa-3-azabicyclo[13.3.0]octadecan-8-yl]oxy]-4-(dimethylamino)-6-methyl-tetrahydropyran-3-yl] benzoate

[(2S,3R,4S,6R)-4-(dimethylamino)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] benzoate (Example 2) (250.mg, 0.3600 mmol) was mixed with Carbonyldiimidazole (466.73 mg, 2.88 mmol) and Triethylamine (291.27 mg, 2.88 mmol) in THE (2.5 mL). After stirring for 2 days the intermediate product was isolated by portioning between DCM and saturated sodium hydrogen carbonate solution. The DCM phase was dried over magnesium sulphate and concentrated under reduced pressure. DMF (1 mL) was added followed by Benzylamine (46.26 mg, 0.4300 mmol) and 1,8-Diazabicyclo[5.4.0]undec-7-ene (65.73 mg, 0.4300 mmol). When no starting material was left the material was again portioned between DCM and saturated sodium hydrogen carbonate solution. The DCM phase was again dried over magnesium sulphate and concentrated under reduced pressure. The material was dissolved in acetonitrile and purified by reversed phase chromatography (see general methods). The clean fractions were concentrated and lyophilized to a solid.

Example 5: (2R,3S,4R,5R,8R,10R,11R,12S,13S,14R)-11-[(2S,3R,4S,6R)-4-[benzyl(methyl)amino]-3-hydroxy-6-methyl-tetrahydropyran-2-yl]oxy-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-1-oxa-6-azacyclopentadecan-15-one

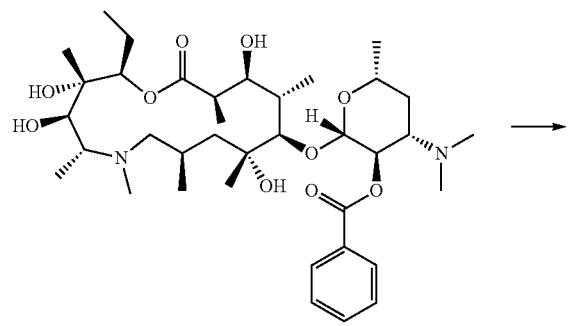 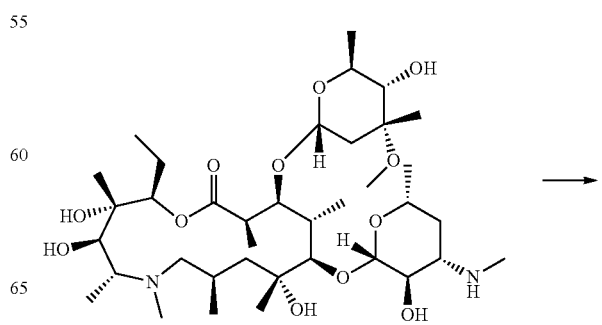

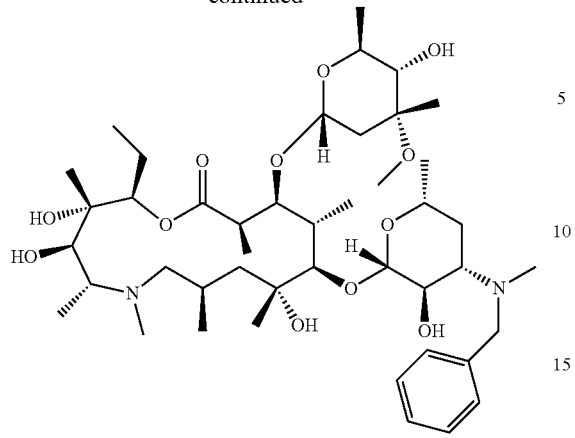
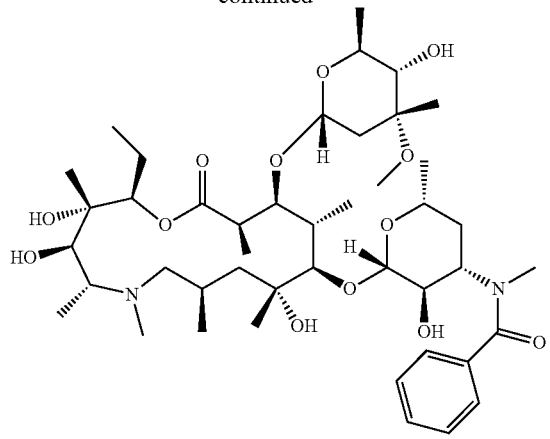

Intermediate A is (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one. That compound was prepared by N-demethylation of azithromycin using the method as set out in U.S. Pat. No. 3,725,385, also described in *European Journal of Medicinal Chemistry* 49 (2012) 365-378, entry 5.1.3. Benzyl bromide (43.63 mg, 0.2600 mmol) was added to a mixture of ((2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one) (Intermediate A) (125.mg, 0.1700 mmol) and N,N-Diisopropylethylamine (32.97 mg, 0.2600 mmol) in IPA (1 mL). When no starting material was observed the reaction was portioned between DCM and sodium hydrogen carbonate solution. The DCM was removed under reduced pressure and the residue was dissolved in acetonitrile and purified using reversed phase chromatography (see general methods). The clean fractions were combined and concentrated followed by lyophilization to obtain the product as a solid.

Example 6: N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-3-hydroxy-6-methyl-tetrahydropyran-4-yl]-N-methylbenzamide

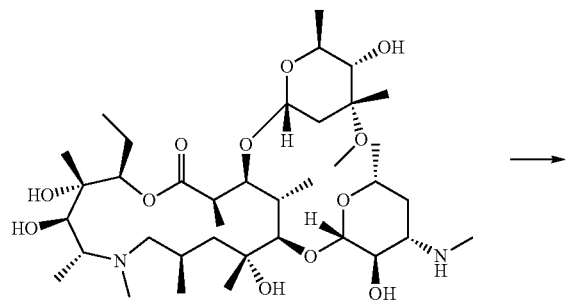

Benzoyl chloride (27.83 mg, 0.2000 mmol) was added to a mixture of (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (97.mg, 0.1300 mmol) (Intermediate A) and Sodium hydrogen carbonate (16.63 mg, 0.2000 mmol) in IPA (1 mL). When no starting material was left the mixture was portioned between saturated sodium hydrogen carbonate and DCM. The solvent was removed under reduced pressure and the residue was diluted with acetonitrile and purified using reversed phase chromatography (see general methods) concentration and lyophilization gave the product as a solid.

Example 7: N-[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-benzamide

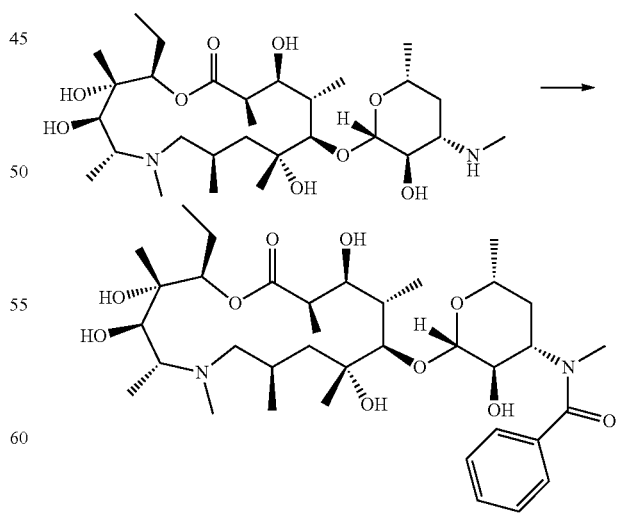

Intermediate B is (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]

oxy-3,5,6,8,10,12,14-heptamethyl-1-oxa-6-azacyclopentadecan-15-one. That compound was prepared by N-demethylation of des-cladinose azithromycin (Example 1) using the method as set out in U.S. Pat. No. 3,725,385, also described in *European Journal of Medicinal Chemistry* 49 (2012) 365-378, entry 5.1.3.

Benzoyl chloride (20.96 mg, 0.1500 mmol) was added to a mixture of (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (57.33 mg, 0.1000 mmol) and Sodium hydrogen carbonate (12.53 mg, 0.1500 mmol) in IPA (1.25 mL). When no starting material was left the mixture was portioned between saturated sodium hydrogen carbonate and DCM. The solvent was removed under reduced pressure and the residue was diluted with acetonitrile and purified using reversed phase chromatography (see general methods) concentration and lyophilization gave the product as a solid.

Example 8: N-[(2S,3R,4S,6R)-2-[[(2R,3S,4R,5R, 8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-naphthalene-2-sulfonamide

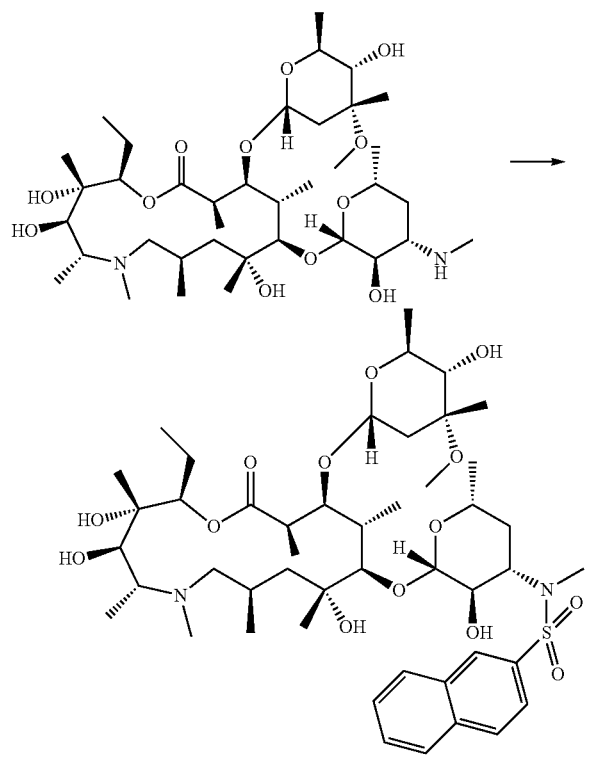

To (2R,3S,4R,5R,8R,10R,11R,12S,13S,14R)-2-ethyl-3,4, 10-trihydroxy-13-[(2R,4R,5S,6S)-5-hydroxy-4-methoxy-4, 6-dimethyl-tetrahydropyran-2-yl]oxy-11-[(2S,3R,4S,6R)-3-hydroxy-6-methyl-4-(methylamino)tetrahydropyran-2-yl] oxy-3,5,6,8,10,12,14-heptamethyl-1-oxa-6-azacyclopentadecan-15-one (Intermediate A) (195.mg, 0.2700 mmol) 200 mg (containing ca 50% of the desired starting material as well as the non demethylated material), Sodium hydrogen carbonate (33.43 mg, 0.4000 mmol) and 2-Naphthalenesulfonyl chloride (90.21 mg, 0.4000 mmol) was added THF (1 mL) and IPA (1 mL). The reaction was stirred over night and good conversion to the desired product was obtained. The reaction was worked up by adding DCM and saturated sodium hydrogen carbonate solution. The organic phase was collected and concentrated to a yellow oil. The crude product was dissolved in ca 4 ml of ACN and filtered and chromatographed on preparative LC (see general information) to give pure product fractions that were concentrated and lyophilized to a solid material.

Example 9: N-[(2S,3R,4S,6R)-2-[[(2R,3S,4R,5R, 8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-naphthalene-2-sulfonamide

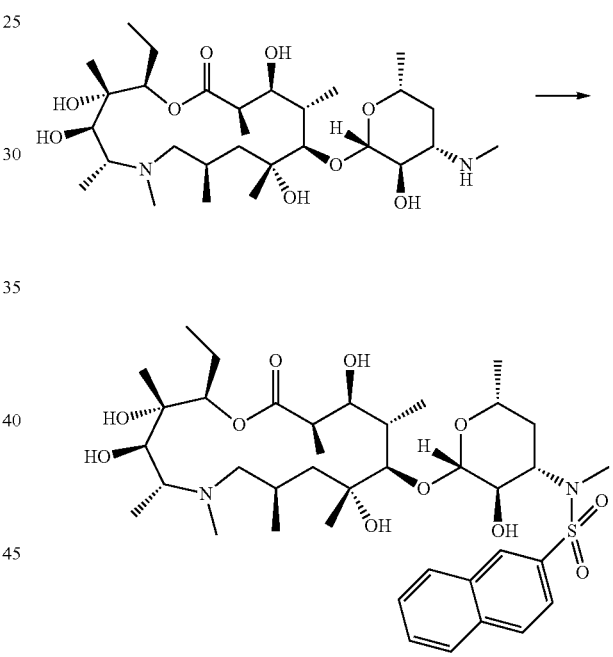

To (2R,3 S,4R,5R,8R,10R,11R,12S,13 S,14R)-2-ethyl-3, 4,10,13-tetrahydroxy-11-[(2S,3R,4S,6R)-3-hydroxy-6-methyl-4-(methylamino)tetrahydropyran-2-yl]oxy-3,5,6,8, 10,12,14-heptamethyl-1-oxa-6-azacyclopentadecan-15-one (Intermediate B) (175.mg, 0.3000 mmol) (containing ca 50% of the desired starting material as well as the non demethylated material), Sodium hydrogen carbonate (38.24 mg, 0.4600 mmol) and 2-Naphthalenesulfonyl chloride (103.17 mg, 0.4600 mmol) was added IPA (2 mL). The reaction was stirred overnight. The reaction was worked up by adding DCM and saturated sodium hydrogen carbonate solution. The organic phase was collected and concentrated. The crude product was dissolved in ca 4 ml of ACN and filtered and separated on preparative LC (see general information) to give pure product fractions that were concentrated and lyophilized to a solid material.

Example 10: N-[(2S,3R,4S,6R)-2-[[(2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-3,5,6,8,10,12,14-heptamethyl-15-oxo-1-oxa-6-azacyclopentadec-11-yl]oxy]-3-hydroxy-6-methyl-tetrahydropyran-4-yl]-N,4-dimethyl-benzenesulfonamide

Example 11: [(2S,3R,4S,6R)-2-[[(2R,3R,4R,5R,8R,10R,11R,12S,13S,14R)-4,13-diacetoxy-2-ethyl-3,10-dihydroxy-3,5,6,8,10,12,14-heptamethyl-15-oxo-1-oxa-6-azacyclopentadec-11-yl]oxy]-4-(dimethylamino)-6-methyl-tetrahydropyran-3-yl] benzoate

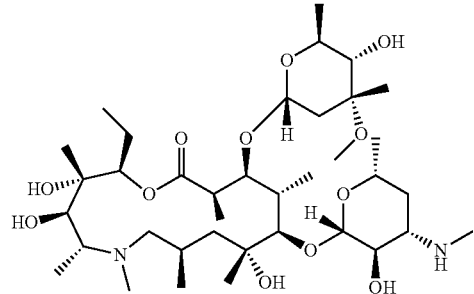

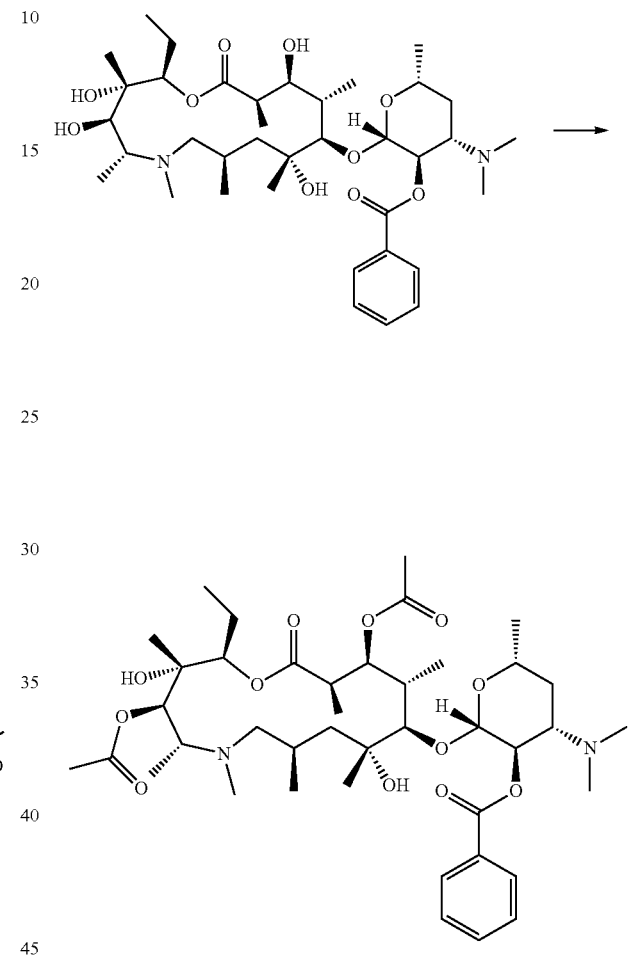

To (2R,3S,4R,5R,8R,10R,11R,12S,13S,14R)-2-ethyl-3,4,10-trihydroxy-13-[(2R,4R,5S,6S)-5-hydroxy-4-methoxy-4,6-dimethyl-tetrahydropyran-2-yl]oxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate A) (199.98 mg, 0.2700 mmol) (containing ca 50% of the desired starting material as well as the non demethylated material), Sodium hydrogen carbonate (34.29 mg, 0.4100 mmol) and p-Toluenesulfonyl chloride (77.81 mg, 0.4100 mmol) was added IPA (2 mL). The reaction was stirred overnight (the conversion and purity was not as good as the 2-naphtyl analogue). The reaction was worked up by adding DCM and saturated sodium hydrogen carbonate solution. The organic phase was collected and concentrated. The crude product was dissolved in ca 4 ml of ACN and filtered and separated on preparative LC (see general information) to give pure product fractions that were concentrated and lyophilized to a solid material.

To a solution of [(2S,3R,4S,6R)-4-(dimethylamino)-2-[[(2R,3S,4R,5R,8R, 10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] benzoate (Example 2) (200.mg, 0.2900 mmol) in DCM (2 mL), acetic anhydride (146.91 mg, 1.44 mmol) and Pyridine (113.82 mg, 1.44 mmol) was added. The mixture was stirred until the main product was the di acetylated. The mixture was worked up by addition of saturated sodium hydrogen carbonate solution approximately the same volume as the reaction mixture. The organic phase was concentrated and dissolved in acetonitrile (ca 4 ml). The solution was filtered and purified on reversed phase chromatography (see general methods). The clean fractions were collected and concentrated under reduced pressure and lyophilized to give the product as a solid.

Example 12: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-(4-methylsulfonylphenyl) benzoate)

Example 13: [(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-4-[methyl(2-naphthylsulfonyl)amino]tetrahydropyran-3-yl] benzoate)

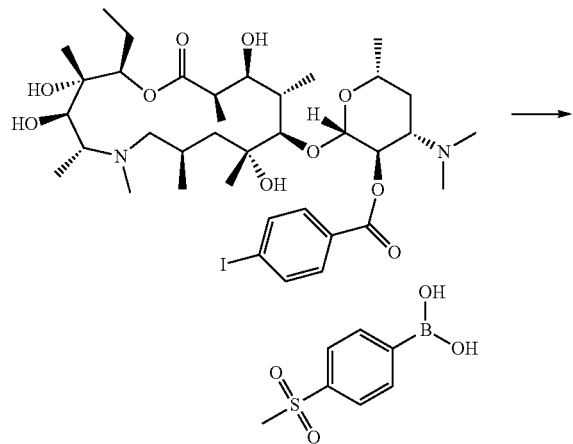

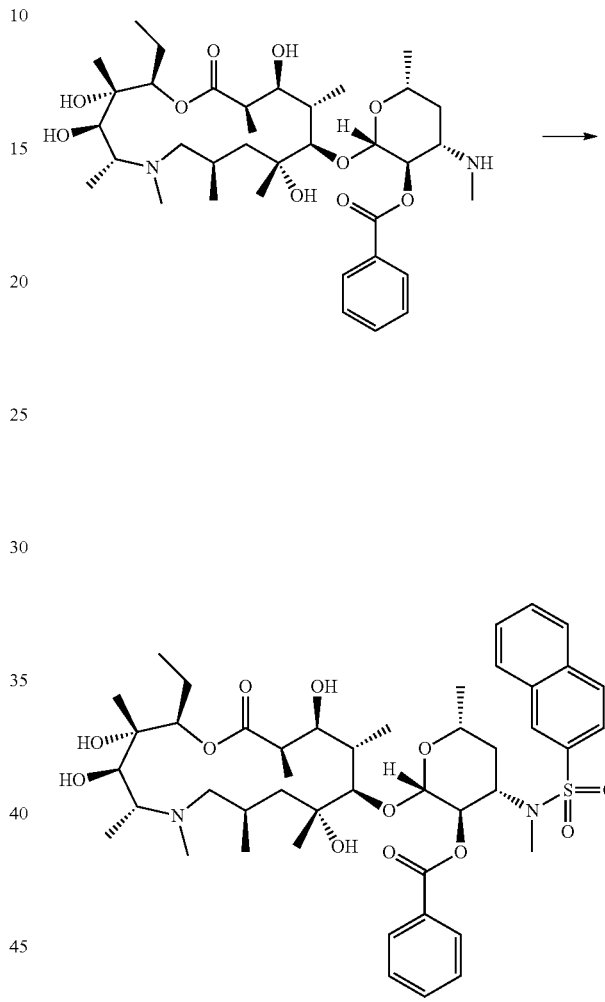

To an inert (nitrogen flushed) mixture of [(2S,3R,4S,6R)-4-(dimethylamino)-2-[[(2R,3 S,4R,5R,8R,10R,11R,12S,13 S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-iodobenzoate (Example 14) (200.mg, 0.2400 mmol), Potassium carbonate (101.05 mg, 0.7300 mmol), Bis(triphenylphosphine)palladium(II) dichloride (8.55 mg, 0.0100 mmol) and (4-methylsulfonylphenyl)boronic acid (73.12 mg, 0.3700 mmol) was added water 0.2 ml and DME (2 ml). The mixture was heated to 60 degrees. when there was no starting material left the reaction was worked up by portioning between saturated sodium hydrogen carbonate solution and DCM. The DCM phase was concentrated and the mixture was dissolved in acetonitrile, filtered and purified on reversed phase chromatography (see general methods). the clean fractions were concentrated and lyophilized to give the product as a solid.

[(2S,3R,4S,6R)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-4-(methylamino)tetrahydropyran-3-yl] benzoate (Example 2) (150.mg, 0.2200 mmol) was mixed with 2-Naphthalenesulfonyl chloride (59.93 mg, 0.2600 mmol) in IPA (1.5 mL). Sodium hydrogen carbonate (24.06 mg, 0.2900 mmol) was added as an acid scavenger. The reaction was very quick and after ca 30 min the mixture was portioned between DCM and saturated sodium hydrogen carbonate solution. The organic phase was concentrated and diluted with acetonitrile. The mixture was filtered and purified by reversed phase chromatography (see general information). The clean fractions were concentrated and lyophilized to give the product as a solid.

Example 14: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-iodobenzoate)

Example 15: O1-benzylO5-[(2S,3R,4S,6R)-4-(dimethylamino)-2-[[(2R,3S,4R,5R,8R,10R, 11R,12S, 13S, 14R)-2-ethyl-3,4,10,13-tetrahydroxy-3,5,6,8, 10,12,14-heptamethyl-15-oxo-1-oxa-6-azacyclopentadec-11-yl]oxy]-6-methyl-tetrahydropyran-3-yl] (2R)-2-(benzyloxycarbonylamino) pentanedioate

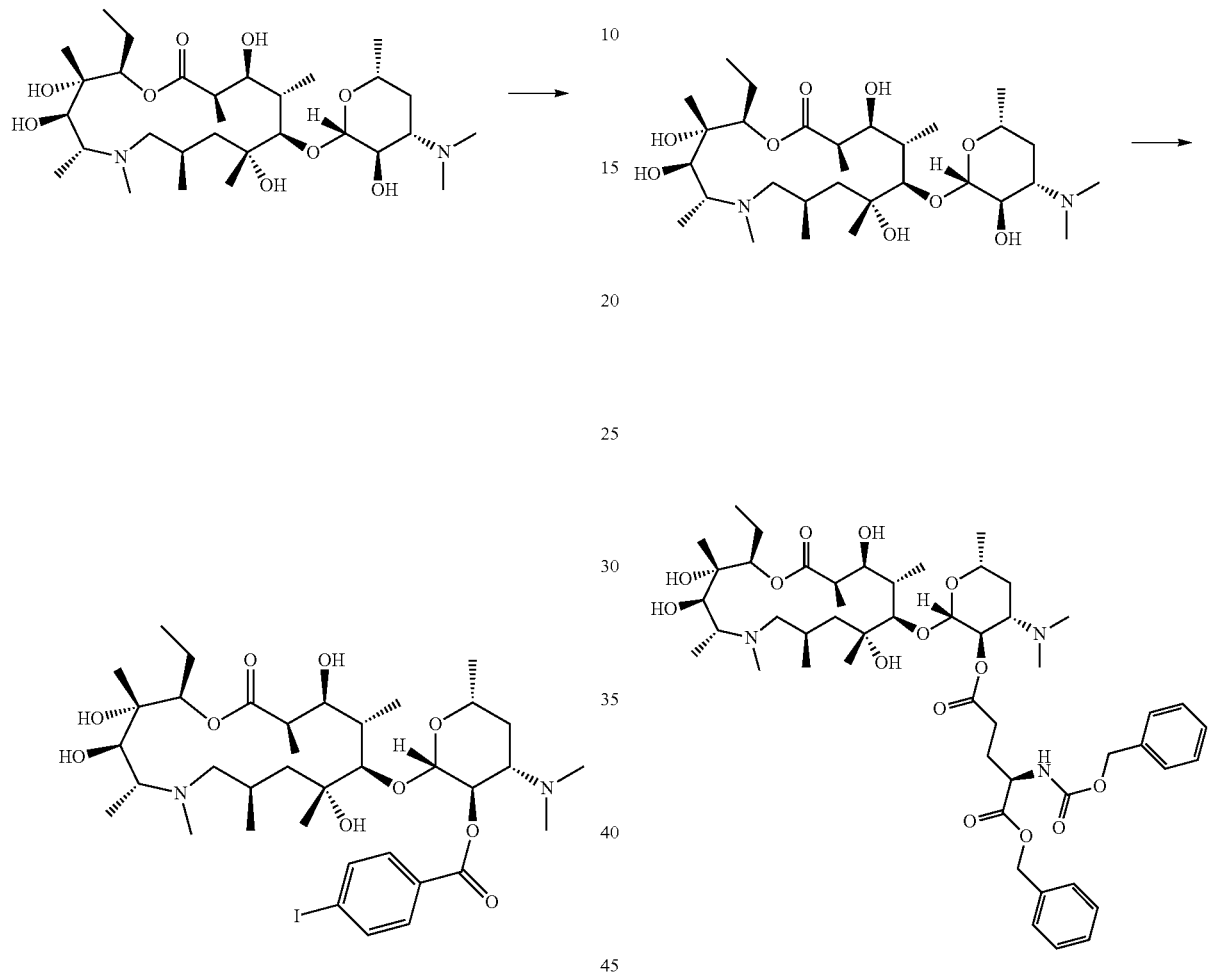

4-Iodobenzoyl chloride (270.61 mg, 1.02 mmol) was added to a mixture of (2R,3S,4R,5R,8R,10R,11R,12S,13S, 14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (500.mg, 0.8500 mmol) and N,N-Diisopropylethylamine (164.07 mg, 1.27 mmol) in THF (5 mL) cooled over ice. After addition the mixture was allowed to reach room temperature. The reaction was stirred for ca 3 h and then portioned between DCM and saturated sodium hydrogen carbonate. The organic phase was dried over magnesium sulphate and concentrated to an off white solid. A portion of the crude was purified by reversed phase chromatography (see general information) and the rest of the material will be used as crude in palladium catalyzed cross coupling reactions.

(2R,3S,4R,5R,8R,10R,11R,12S,13S,14R)-11-[(2S,3R, 4S,6R)-4-(dimethylamino)-3-hydroxy-6-methyl-tetrahydropyran-2-yl]oxy-2-ethyl-3,4,10,13-tetrahydroxy-3,5,6,8,10, 12,14-heptamethyl-1-oxa-6-azacyclopentadecan-15-one (Example 1) (250 mg, 0.4200 mmol) was added to a mixture of Z-D-glutamic acid 1-benzyl ester (235.71 mg, 0.6300 mmol), 4-(Dimethylamino)pyridine (5.17 mg, 0.0400 mmol) and DCC (130.96 mg, 0.6300 mmol) in DCM (2.5 mL). The reaction was stirred over night and water 0.1 ml was added. The reaction was concentrated and diluted to ca 4 ml with acetonitrile, filtered and the product was purified using reversed phase chromatography. (see general methods) The pure fractions were concentrated and the water was removed by lyophilzation giving the title compound as a solid.

Example 16: benzyl (2R)-2-(benzyloxycarbonylamino)-5-[[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-methyl-amino]-5-oxo-pentanoate

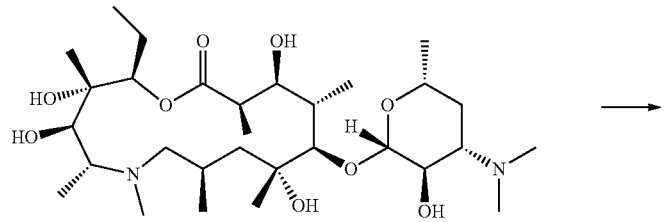

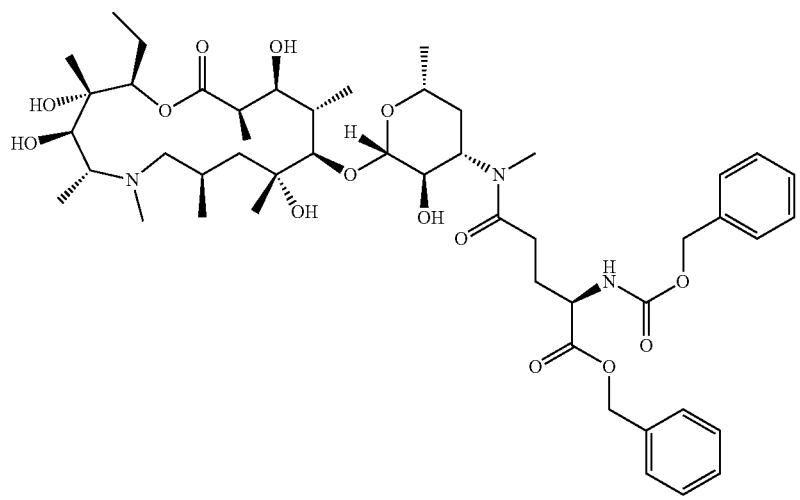

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (300.mg, 0.5100 mmol), EDC hydrochloride (113.93 mg, 0.7600 mmol), and 4-(Dimethylamino)pyridine (6.2 mg, 0.0500 mmol) in DCM (3 mL) was added Z-D-glutamic acid 1-benzyl ester (282.88 mg, 0.7600 mmol) in one portion. The mixture was stirred until the starting material had disappeared (ca 2 h). Water 0.1 ml was added. The reaction was concentrated and diluted to ca 4 ml with acetonitrile, filtered and the product was purified using reversed phase chromatography (see general methods). The pure fractions were concentrated and the water was removed by lyophilzation giving the product as a white solid.

Example 17: 4-[(2S,3R,4S,6R)-4-(dimethylamino)-2-[[(2R,3S,4R,5R,8R,10R,11R,12S, 13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl]oxy-4-oxo-butanoic acid

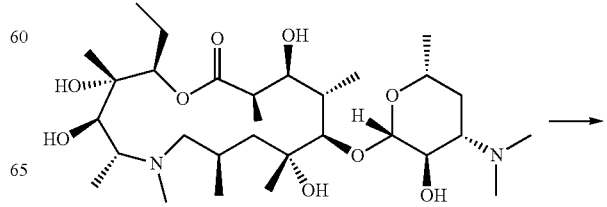

-continued

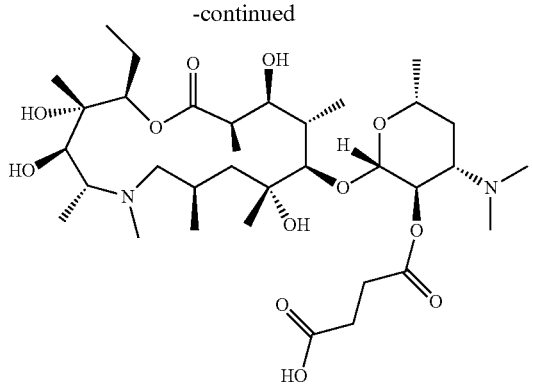

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (250.mg, 0.4200 mmol) and 4-(Dimethylamino)pyridine (5.17 mg, 0.0400 mmol) in DCM (2.5 mL) was added Succinic anhydride (63.52 mg, 0.6300 mmol) in one portion. The mixture was stirred at room temperature over night. The solvent was removed under reduced pressure and the residue was diluted with acetonitrile to a volume of ca 4 ml. The mixture was filtered and purified on reversed phase chromatography (see general methods), the clean fractions were concentrated and lyophilized giving the product as a white solid.

Example 18: Descladinose Azithromycin N-Succinyl 4-[[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-methyl-amino]-4-oxo-butanoic acid

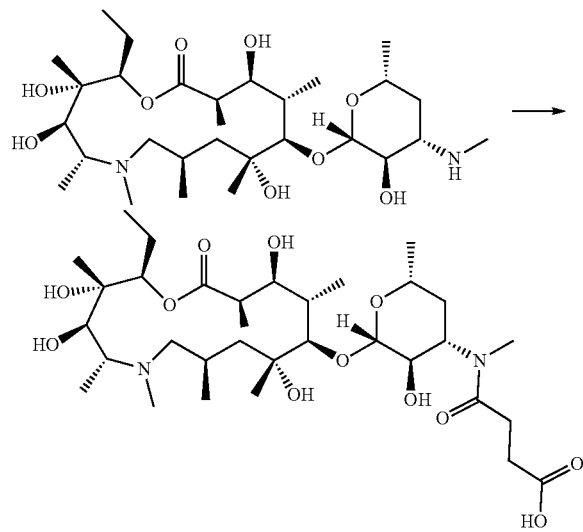

To a solution of (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (300.mg, 0.5200 mmol), (N-demethyl descladinose Azithromycin) and 4-(Dimethylamino)pyridine (6.35 mg, 0.0500 mmol) in DCM (3 mL) was added Succinic anhydride (78.07 mg, 0.7800 mmol) as one portion at RT. The mixture was stirred for ca 2 h and after no starting material was observed (LC) water (0.1 ml) was added to the mixture. The solution was concentrated under reduced pressure and acetonitrile was added to a volume of ca 4 ml. The mixture was filtered and purified on reversed phase chromatography (see general methods). The clean fractions were collected and concentrated followed by lyophilization to give the product as a white solid.

Example 19: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] pyridine-3-carboxylate)

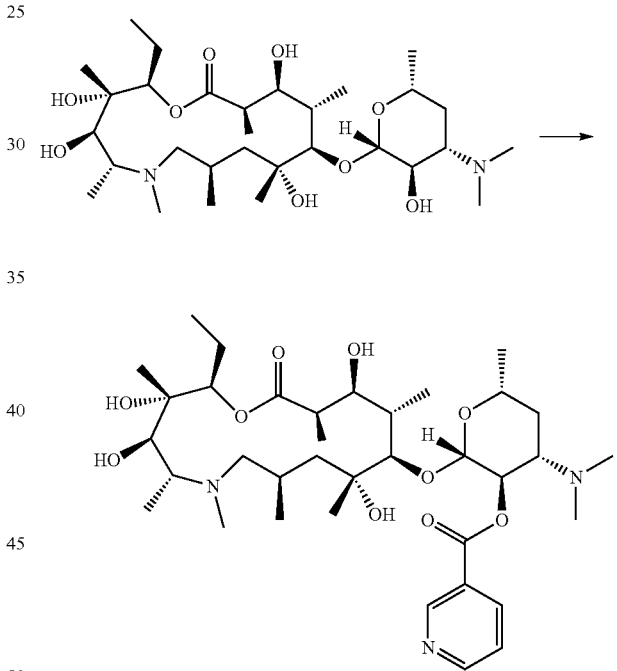

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (250 mg, 0.4200 mmol), nicotinic Acid (78.15 mg, 0.6300 mmol) and 4-(Dimethylamino)pyridine (12.93 mg, 0.1100 mmol) in DCM (2.5 mL), DCC (130.98 mg, 0.6300 mmol) was added in one portion. The mixture was stirred at room temperature over night. The solvent was removed under reduced pressure and the residue was diluted with acetonitrile to a volume of ca 4 ml. The mixture was filtered and purified on reversed phase chromatography (see general methods), the clean fractions were concentrated and lyophilized giving the product as a white solid.

Example 20: [(2S,3R,4S,6R)-4-(dimethylamino)-2-[[(2R,3S,4R,5R,8R,10R,11R,12S, 13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 2,5-dimethylpyrazole-3-carboxylate Example 21: [(2S,3R,4S,6R)-4-(dimethylamino)-2-[[(2R,3S,4R,5R,8R,10R,11R,12S, 13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 5-chlorothiophene-2-carboxylate

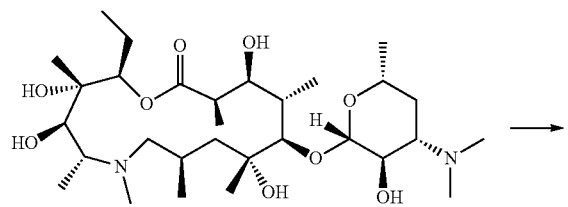

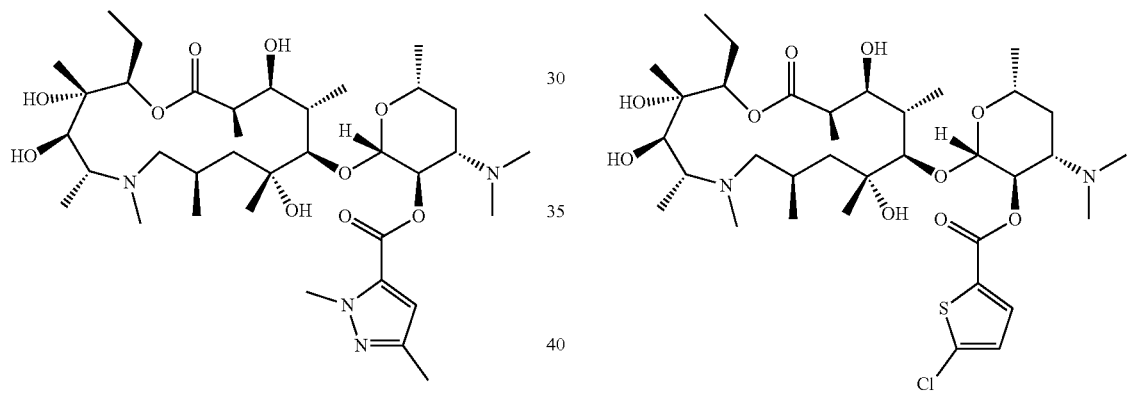

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (210.mg, 0.3600 mmol), EDC hydrochloride (79.76 mg, 0.5300 mmol), and 4-(Dimethylamino)pyridine (21.72 mg, 0.1800 mmol) in DCM (2.5 mL) was added 1,3-Dimethyl-1H-pyrazole-5-carboxylic acid (74.73 mg, 0.5300 mmol) in one portion. The mixture was stirred over night at room temperature. The reaction was quenched by addition of ca 0.1 ml of water, concentrated and diluted to ca 4 ml with acetonitrile. The mixture was filtered and the product purified using reversed phase chromatography (see general methods). The pure fractions were concentrated under reduced pressure (to remove the main part of the acetonitrile) and the water was removed by lyophilzation giving the product as a white solid.

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (210.mg, 0.3600 mmol), EDC hydrochloride (79.76 mg, 0.5300 mmol), and 4-(Dimethylamino)pyridine (21.72 mg, 0.1800 mmol) in DCM (2.5 mL) was added 5-Chlorothiophene-2-carboxylic acid (86.7 mg, 0.5300 mmol) in one portion. The mixture was stirred over night at room temperature. Water 0.1 ml was added. The reaction was concentrated and diluted to ca 4 ml with acetonitrile. The material was filtered prior to purification using reversed phase chromatography (see general methods). The pure fractions were concentrated under reduced pressure and the water was removed by lyophilzation giving the product as a white solid.

Example 22: [(2S,3R,4S,6R)-4-(dimethylamino)-2-[[(2R,3S,4R,5R,8R,10R,11R,12S, 13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-ethylbenzoate Example 23: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 4-methoxybenzoate

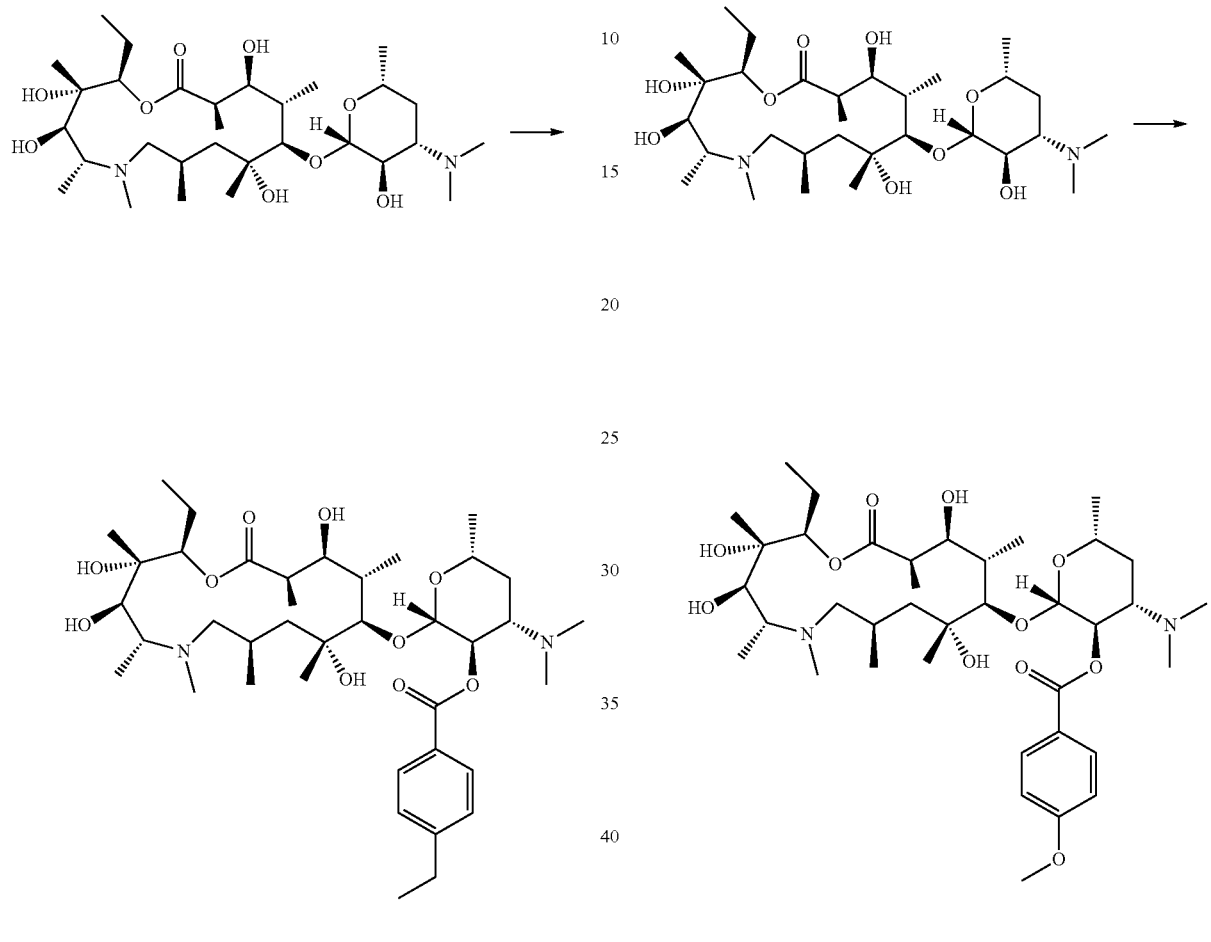

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (242.mg, 0.4100 mmol), EDC hydrochloride (91.9 mg, 0.6100 mmol), and 4-(Dimethylamino)pyridine (25.02 mg, 0.2000 mmol) in DCM (2.5 mL) was added 4-Ethylbenzoic acid (92.27 mg, 0.6100 mmol) in one portion. The mixture was stirred over night at room temperature. Water (0.1 ml) was added to quench the reaction. The reaction was concentrated and diluted to ca 4 ml with acetonitrile, filtered and the product was purified using reversed phase chromatography (see general methods). The pure fractions were concentrated under reduced pressure and the water was removed by lyophilzation giving the product as a white solid.

To a mixture of (2R,3S,4R,5R,8R,10R,11R,12S,13S, 14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (226.mg, 0.3800 mmol), EDC hydrochloride (85.82 mg, 0.5700 mmol), and 4-(Dimethylamino)pyridine (23.37 mg, 0.1900 mmol) in DCM (2.5 mL) was added 4-Methoxybenzoic acid (87.3 mg, 0.5700 mmol) in one portion. The mixture was stirred over night at room temperature. Water (0.1 ml) was added to the reaction. The reaction was then concentrated and diluted to ca 4 ml with acetonitrile, filtered and the product was purified using reversed phase chromatography (see general methods). The pure fractions were concentrated under reduced pressure to remove the acetonitrile and the remaining water was removed by lyophilzation giving the product as a white solid.

Example 24: [(2S,3R,4S,6R)-4-(dimethylamino)-2-[[(2R,3S,4R,5R,8R,10R,11R,12S, 13S,14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] naphthalene-2-carboxylate Example 25: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] quinoline-3-carboxylate

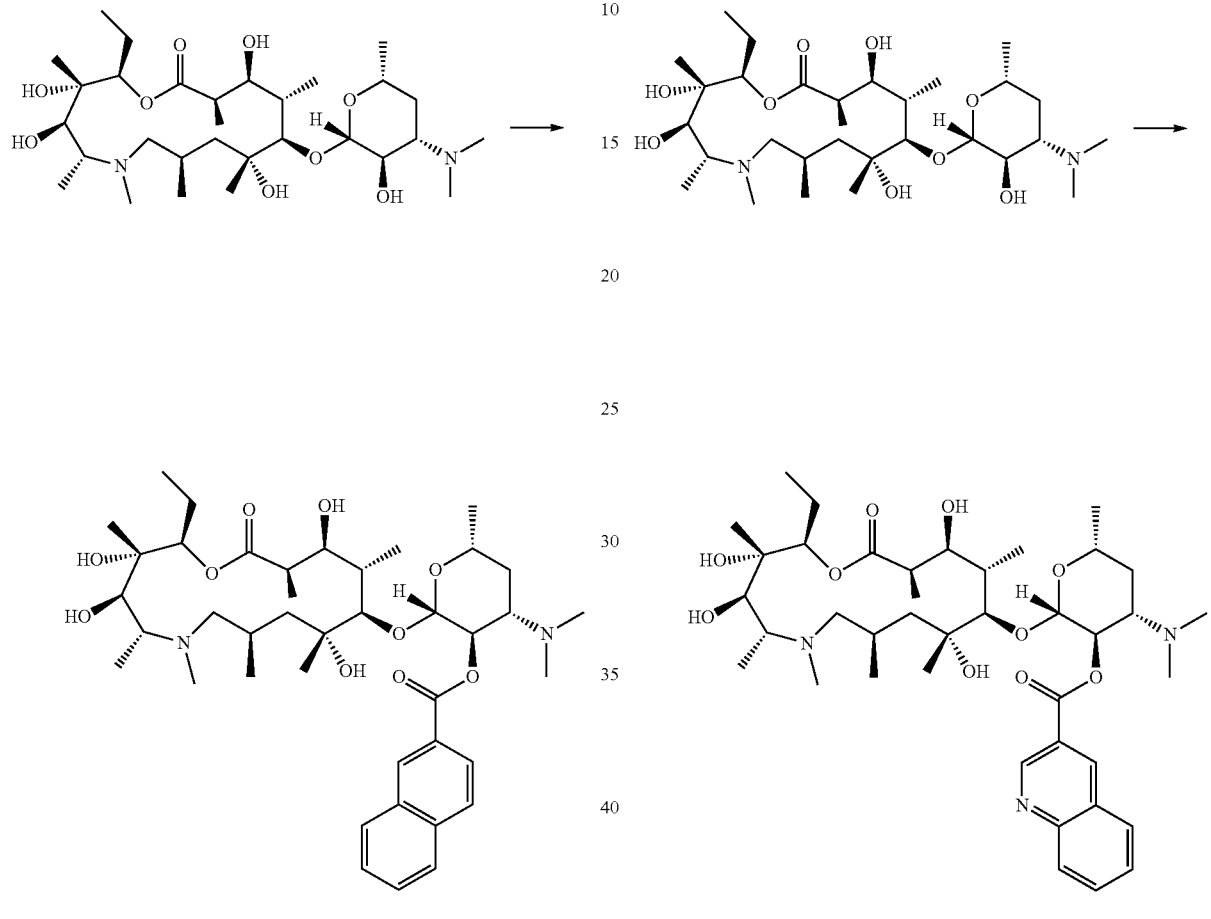

To a mixture of (2R,3S,4R,5R,8R,10R,11R,12S,13S,14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (231.mg, 0.3900 mmol), EDC hydrochloride (87.72 mg, 0.5900 mmol), and 4-(Dimethylamino)pyridine (23.88 mg, 0.2000 mmol) in DCM (2.5 mL) was added 2-Naphthalenecarboxylic acid (100.98 mg, 0.5900 mmol) in one portion. The mixture was stirred over night at room temperature. Water ca 0.1 ml was added. The reaction was concentrated and diluted to ca 4 ml with acetonitrile. The mixture was filtered and the product was purified using reversed phase chromatography (see general methods). The pure fractions were concentrated under reduced pressure and the water was removed by lyophilzation giving the product as a white solid.

To a mixture of (2R,3S,4R,5R,8R,10R,11R,12S,13S, 14R)-11-[(2S,3R,4S,6R)-4-(dimethylamino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (218.mg, 0.3700 mmol), EDC hydrochloride (82.79 mg, 0.5500 mmol), and 4-(Dimethylamino)pyridine (22.54 mg, 0.1800 mmol) in DCM (2.5 mL) was added 3-Quinolinecarboxylic acid (95.85 mg, 0.5500 mmol) in one portion. The mixture was stirred over night at room temperature. Water 0.1 ml was added. The reaction was concentrated and diluted to ca 4 ml with acetonitrile, filtered and the product was purified using reversed phase chromatography (see general methods). The pure fractions were concentrated under reduced pressure in order to remove the acetonitrile and the water was removed by lyophilzation giving the product as a white solid.

47

Example 26: 2-benzyloxy-N-[(2S,3R,4S,6R)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-acetamide

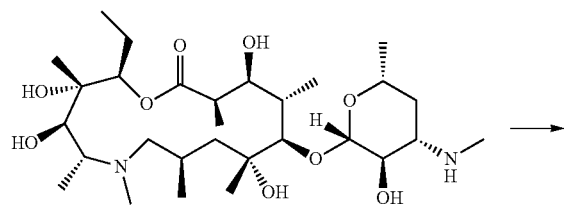

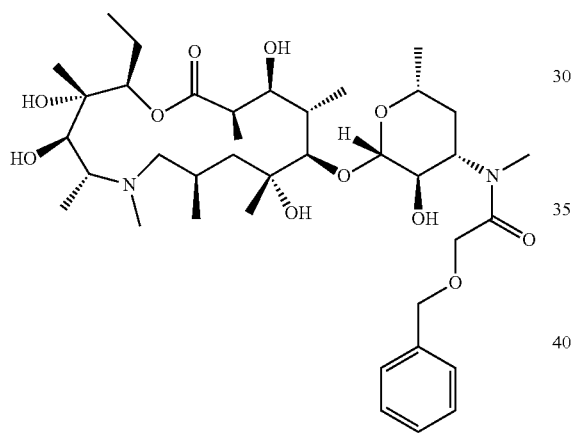

To a mixture of (2R,3S,4R,5R,8R,10R,11R,12S,13S, 14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (254.mg, 0.4400 mmol), EDC hydrochloride (98.8 mg, 0.6600 mmol), and 4-(Dimethylamino)pyridine (26.9 mg, 0.2200 mmol) in DCM (2.5 mL) was added benzyloxyacetic acid (109.77 mg, 0.66 mmol) in one portion. The mixture was stirred over night at room temperature. Water 0.1 ml was added in order to quench excess reagent. The reaction was concentrated and diluted to ca 4 ml with acetonitrile, filtered and the product was purified using reversed phase chromatography (see general methods). The pure fractions were concentrated under reduced pressure and the water was removed by lyophilzation giving the product as a white solid.

48

Example 27: Benzyl N-[2-[[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-methyl-amino]-2-oxo-ethyl]carbamate

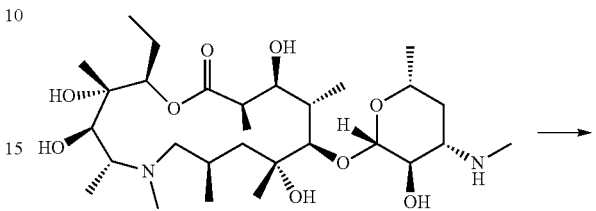

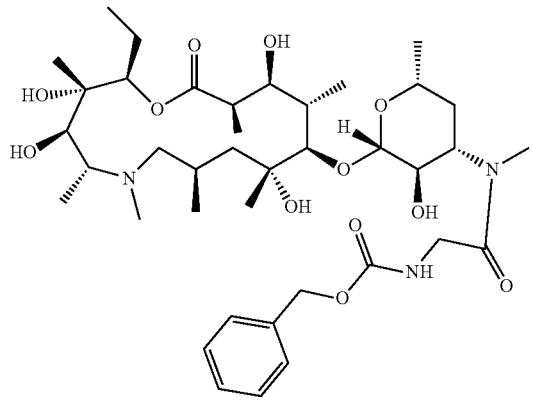

To a mixture of (2R,3S,4R,5R,8R,10R,11R,12S,13S, 14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (241 mg, 0.4200 mmol), EDC hydrochloride (93.75 mg, 0.6300 mmol), and 4-(Dimethylamino)pyridine (25.52 mg, 0.2100 mmol) in DCM (2.5 mL) cooled over ice, was added Z-Glycine (131.12 mg, 0.6300 mmol) in one portion. The mixture was allowed to reach room temperature and was stirred over night. Water 0.1 ml was added. The reaction was concentrated and diluted to ca 4 ml with acetonitrile, filtered and the product was purified using reversed phase chromatography (see general methods). The pure fractions were concentrated under reduced pressure and the water was removed by lyophilzation to give the product as a white solid.

Example 28: N-[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-3-phenoxypropanamide

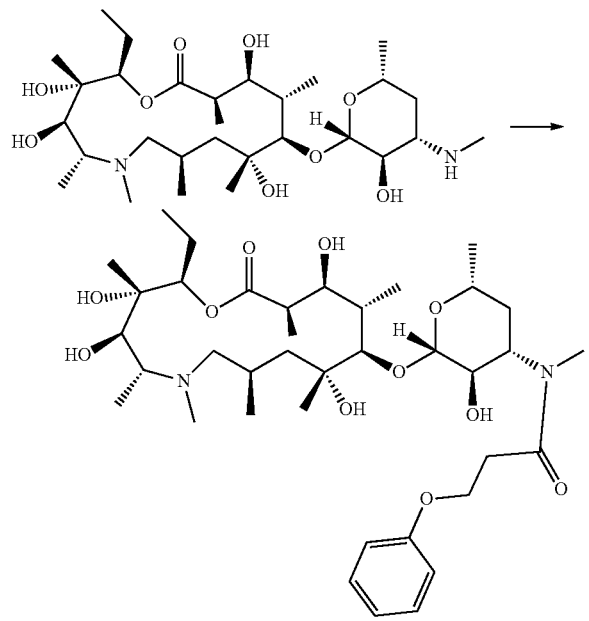

To a mixture (cooled on ice) of (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (286.mg, 0.5000 mmol), EDC hydrochloride (111.25 mg, 0.7400 mmol), and 4-(Dimethylamino)pyridine (30.29 mg, 0.2500 mmol) in DCM (2.5 mL) was added 3-Phenoxypropionic acid (123.6 mg, 0.7400 mmol) in one portion. The mixture was stirred over night at room temperature. Water (ca 0.1 ml) was added to quench the reaction. The reaction was concentrated and diluted to ca 4 ml with acetonitrile, filtered and the product was purified using reversed phase chromatography (see general methods). The pure fractions were concentrated under reduced pressure and the water was removed by lyophilzation giving the product as a white solid.

Example 29: N-[(2S,3R,4S,6R)-2-[[(2R,3S,4R,5R,8R,10R,11R,12S,13S,14R)-2-ethyl-3,4,10,13-tetrahydroxy-3,5,6,8,10,12,14-heptamethyl-15-oxo-1-oxa-6-azacyclopentadec-11-yl]oxy]-3-hydroxy-6-methyl-tetrahydropyran-4-yl]-N-methyl-2-phenylacetamide

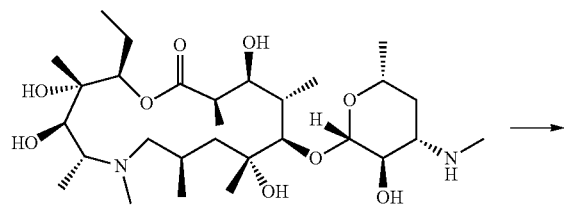

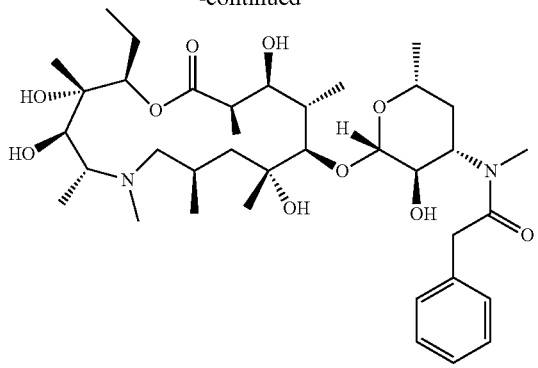

To a solution of (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (246.mg, 0.4300 mmol) in DCM (2.5 mL) cooled on ice was Phenylacetyl chloride (98.9 mg, 0.6400 mmol) carefully added. The resulting mixture was allowed to reach room temperature and after ca 1 h the reaction was quenched by addition of a couple of drops of water. The solvent was removed and acetonitrile was added to ca 4 ml total volume. The mixture was filtered and purified using reversed phase chromatography (see general methods). The solvent was removed at reduced pressure and the resulting water was removed by freeze drying giving the product as a white solid.

Example 30: (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one

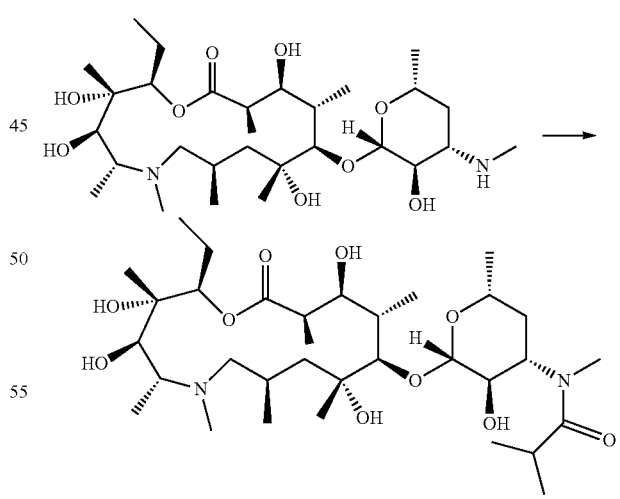

To a solution of (2R,3S,4R,5R,8R,10R,11R,12S,13S,14R)-2-ethyl-3,4,10,13-tetrahydroxy-11-[(2S,3R,4S,6R)-3-hydroxy-6-methyl-4-(methylamino)tetrahydropyran-2-yl]oxy-3,5,6,8,10,12,14-heptamethyl-1-oxa-6-azacyclopentadecan-15-one (Intermediate B) (249.mg, 0.4300 mmol) in DCM (2.5 mL) cooled on ice was Isobutyryl chloride (69.mg, 0.6500 mmol) carefully added. The resulting mixture was allowed to reach room temperature and after ca 1 h the reaction was quenched by addition of a couple of drops of water. The solvent was removed and acetonitrile was added to ca 4 ml total volume. The mixture was filtered and purified using reversed phase chromatography (see general methods). The solvent was removed at reduced pressure and the resulting water was removed by freeze drying giving the product as a white solid Example 31: [(2S,3R,4S,6R)-4-(dimethylamino)-2-[[(2R,3S,4R,5R,8R,10R,11R,12S,13S, 14R)-2-ethyl-3,4,10,13-tetrahydroxy-3,5,6,8,10,12,14-heptamethyl-15-oxo-1-oxa-6-azacyclopentadec-11-yl]oxy]-6-methyl-tetrahydropyran-3-yl] 2-methylpropanoate

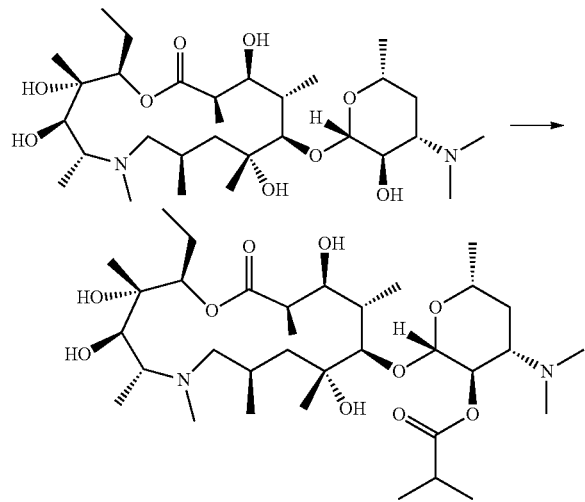

To a mixture of (2R,3S,4R,5R,8R,10R,11R,12S,13S, 14R)-11-[(2S,3R,4S,6R)-4-(dimethyl-amino)-3-hydroxy-6-methyl-tetrahydropyran-2-yl]oxy-2-ethyl-3,4,10,13-tetrahydroxy-3,5,6,8,10,12,14-heptamethyl-1-oxa-6-azacyclopentadecan-15-one (Example 1) (231.mg, 0.3900 mmol) and 4-(Dimethylamino)pyridine (23.88 mg, 0.2000 mmol) in DCM (2.5 mL) was added Isobutyryl chloride (62.49 mg, 0.5900 mmol) in one portion. The mixture was stirred over night at room temperature. Water 0.1 ml was added. The reaction was concentrated and diluted to ca 4 ml with acetonitrile, filtered and the product was purified using reversed phase chromatography (see general methods). The pure fractions were concentrated under reducer pressure and the water was removed by lyophilzation giving the product as a white solid.

Testing of Compounds

Example A: Antimicrobial Activity

The antimicrobial activity of each Example compound was investigated. The Minimal Inhibitory Concentration (MIC—the minimal dose required to inhibit bacterial growth) and the Minimal Bactericidal Concentration (MBC—the minimal dose required to kill bacteria) were measured for each compound for *Streptococcus pneumoniae* (ATCC49619), *Staphylococcus aureus* (ATCC29213), *Bacillus megaterium* (BM-11) and *Escherichia coli* (D-21) using an antimicrobial broth dilution method on microtiter plates. The Minimal Inhibitory Concentration (MIC) was also measured for each example compound and azithromycin with *Mycobacterium avium* complex (MAC). *Mycobacterium avium* complex (MAC) is a term that covers both *M avium* and *M. intracellulare*.

Assay 1:

The antibacterial activities of example compounds 1 to 31 and azithromycin were investigated. The Minimal Inhibitory Concentration (MIC—the minimal dose required to inhibit bacterial growth) and the Minimal Bactericidal Concentration (MBC—the minimal dose required to kill bacteria) were measured for each compound for *Streptococcus pneumoniae* (ATCC49619), *Staphylococcus aureus* (ATCC29213), *Bacillus megaterium* (BM-11) and *Escherichia coli* (D-21) using an antimicrobial broth dilution method on 96 well microtiter plates.

A 256 µg/ml stock solution of each compound was prepared in Mueller-Hinton Broth and then further diluted by a 2-fold serial dilution. The serial dilution was performed on a 96 well microtiter plate to leave 50 µl of diluted compound per well. Each compound was diluted in duplicate. The compounds to be incubated with *Streptococcus pneumoniae* (ATCC49619) were diluted in Mueller-Hinton broth containing 5% horse blood and 20 ml/L ONAD.

The bacterial cultures were diluted with sterile saline to give a solution with a value of 0.5 on the McFarland turbidity standard. This solution was then further diluted (1:100) in Mueller-Hinton Broth. 50 µl of diluted culture was added to each well of the 96 well plate to give a cell density of approximately $10^6$ cells/ml and final assay volume of 100 µl. After addition of the bacterial solution the final concentration range of the compounds was 128, 64, 32, 16, 8, 4, 2, 1, 0.5 and 0.25 µg/ml. The compounds were also tested at the higher concentrations of 500 and 1000 µg/ml. The controls included wells containing only broth and bacteria, and wells containing only broth.

After addition of the bacterial solution, the plates were incubated at 35° C. for 18 h. The bacterial growth of each well was then recorded and then the Minimal Inhibitory Concentration (MIC) and Minimal Bactericidal Concentration (MIB) were determined.

Assay 2:

The Minimal Inhibitory Concentration (MIC) was measured for example compounds and azithromycin with *Mycobacterium avium* complex (MAC). *Mycobacterium avium* complex (MAC) is a term that covers both *M. avium* and *M. intracellulare*. The sensitivity of MAC to the test compounds was assessed using the 2,3-diphenyl-5-thienyl-(2)-tetrazolium chloride (STC) colorimetric microplate assay described by Park et al (J Korean Med Sci. 2009, 24(3), 511-2).

Each compound was tested in duplicate with two different strains of *M. avium* (S1002170205 and S1003050114) and *M. intracellulare* (S1005200018 and S1303150028). All strains were sensitive to Clarithromycin (CLR), the choice drug against MAC infections, but sensitivity to other drugs (amikacine, clofazimine, clarithromycin, ethambutol, oflaoxacin, rifabutin, rifampin and isoniazid) was varied.

A 256 µg/ml stock solution of each compound was prepared in Middlebrook broth and then further diluted by a 2-fold serial dilution. The serial dilution was performed on a 96 well microtiter plate to leave 50 µl of diluted compound per well. Each compound was diluted in duplicate. The Middlebrook broth was supplemented with STC to give a final assay concentration of 50 µg/ml.

The MAC strains were proliferated in Lowenstein TB media for 10 days and transferred into Middlebrook broth and cultured for a further 5 days at 37° C. The bacterial strains were then diluted to give a reading of 1 on the McFarland turbidity standard. The cultures were then further diluted and a total of 50 µl added to each well of the 96 well plate to give a cell density of approximately $10^6$ cells/ml and a final assay volume of 100 µl. After addition of the bacterial solution the final concentration range of the compounds was 128, 64, 32, 16, 8, 4, 2, 1, 0.5 and 0.25 µg/ml. The controls included wells containing only broth and bacteria, and wells containing only broth. For the strains S1002170205 (*M. avium*) and S1303150028 (*M. intracellulare*) the compounds were also tested at the higher concentrations of 250, 500 and 1000 µg/ml.

After 7 days, the bacterial growth was determined by recording the colourimetric change of STC. This data was then used to determine the minimal inhibitory concentration (MIC) for each compound.

Results:

For the antibacterial studies in Assay 1, Azithromycin was found to have MIC and MBC concentrations as follows:

| *Str, pneumoniae* (ATCC49619), | | *S. aureus* (ATCC29213) | | *Bacillus megaterium* (BM-11) | | *E. coli* (D-21) | |
|---|---|---|---|---|---|---|---|
| MIC µg/ml | MBC µg/ml | MIC µg/ml | MBC µg/ml | MIC µg/ml | MBC µg/ml | MIC µg/ml | MBC µg/ml |
| 0.06 | 0.06 | 2 | 8 | 1 | 2 | 4 | 32 |

All Example compounds of the invention had higher MIC or MBC concentrations than Azithromycin for each one of the four bacteria studied. For Example compounds 2, 3, 4, 7, 8, 9, 10, 11, 12, 14, 15, 16, 17, 18, 19, 20, 21, 22, 23, 24, 25, 26, 27, 28, 29, 30 and 31, the MIC or MBC concentration were over 16× the MIC and MBC concentrations of Azithromycin for each one of the four bacteria studied. Example compounds 2, 3, 4, 7, 8, 9, 10, 11, 16, 18, 22, 24, 26, 27, 28, 29 and 30 had MIC and MBC concentrations were over 32× the MIC and MBC concentrations of Azithromycin for each one of the four bacteria studied.

In assay 2, Azithromycin was found to have an MIC (µg/ml) concentration as follows:

| MIC (µg/ml) | | | |
|---|---|---|---|
| *Mycobacterium avium* S1002170205 | *Mycobacterium avium* S1003050114 | *Mycobacterium intracellulare* S1005200118 | *Mycobacterium intracellulare* S1305150028 |
| 16 | 32 | 32 | 4 |

All Example compounds of the invention had higher MIC concentrations than Azithromycin for each one of Mycobacteria studied. For Example compounds 1, 2, 3, 4, 7, 8, 9, 10, 11, 12, 14, 15, 16, 17, 18, 19, 20, 21, 22, 23, 24, 25, 26, 27, 28, 29, 30 and 31, the MIC concentration were over 4× the MIC concentration of Azithromycin for each one of the Mycobacteria studied. For *Mycobacterium avium* S1002170205 and *Mycobacterium intracellulare* S1305150028 the MIC concentrations were, for each compound, over 15× the MIC concentration of Azithromycin for Example compounds 2, 3, 4, 7, 9, 11, 12, 14, 15, 16, 17, 18, 19, 20, 21, 22, 23, 24, 25, 26, 27, 28, 29, 30 and 31.

Example B: Trans-Epithelial Resistance Measurements of Immortalized VA10 or BCi-NS1.1 Cells Cultured at Air-Liquid Interface (ALI) in the Presence of Test Compounds Stock solutions were prepared as follows:

DMEMF12+FBS solution: to 500 ml DMEM/F12 solution (Gibco 11330-032) was added 2.5 ml Pen/Strep (Gibco 15070). A 45 ml aliquot was taken and 5 ml FBS solution was added, to give 10% final concentration of FBS.:

DMEMF12+Ultroser G (UG) solution: to one bottle of UG was added 20 ml sterile Cell Culture Grade water and it was dissolved for 30 minutes in the dark at room temperature. 10 ml of the UG mixture was added to 500 ml DMEM/F-12. 2.5 ml Pen/Strep (Gibco 15070) was added and the solution was stored at 4° C. in the dark. The other 10 ml UG was stored at −20° C. in the dark Collagen: 166 µl acetic acid as combined with 83.3 ml cell culture grade water. Collagen was dissolved in 3-5 ml of this mixture. An entire bottle of collagen (Human Type IV Collagen (Sigma C7521-50 MG)) was added to the acetic acid/water mixture. This 10× stock solution was stored at −20° C. Small portions were diluted in cell culture grade water for 1× working solution. The working and stock solutions were filtered through 0.2 µm pore-size filters.

ALI wells: ALI Transwell Filters: 6.5 mm (Corning 3470), 12 mm (Corning 3460) were used. Enough 1× collagen was added to wells to cover membranes, and they were then incubated for at least an hour, at room temperature, or 37° C. The collagen was aspirated. The membranes were washed with 1×PBS, and then the membranes partially covered with lids were allowed to dry completely (~30 minutes) prior to use.

Procedure:

On Day −2, the BCi-NS1.1/VA10 cells suspended in DMEM/F-12+FBS were transferred onto the upper chamber of each membrane as follows:

6.5 mm wells: BCi-NS1.1 cells 15×$10^4$ cells in 200 µl media 6.5 mm wells: VA10 cells 6×$10^4$ cells in 200 µl media 12 mm wells: BCi-NS1.1 cells 0.5×$10^6$ cells in 500 µl media 12 mm wells: VA10 cells 0.2×$10^6$ cells in 500 µl media DMEM/F-12+FBS media was added to the lower chamber as follows:

6.5 mm wells: 1 ml media 12 mm wells: 1.5 ml media

The cells were stored at 37° C., 5% $CO_2$.

On Day −1, the media were aspirated from lower, then upper chambers. The media in both chambers was then replaced with DMEM/F-12+UG as follows:

6.5 mm wells: 1 ml in lower chamber; 200 µl in upper chamber 12 mm wells: 1.5 ml in lower chamber; 500 µl in upper chamber The membranes were stored at 37° C., 5% $CO_2$ On Day 0, the Trans Epithelial Resistance (TER) was measured. Then the medium was aspirated from lower chambers and replaced in the lower chamber with the test sample under investigation in DMEM/F-12+UG (with same volumes as previously applied). The medium in the upper chambers was then aspirated. The chambers were rinsed 1× with PBS, then aspirated leaving upper chamber liquid-free.

The membranes were stored at 37° C., 5% $CO_2$

The media in the lower chamber were changed every 2 days, and any liquid was aspirated from the upper chamber. The TER was measured every 2 days.

The ratio between the TER in the presence of test compound and the TER in the presence of media+diluent alone was calculated for each compound.

The TER resistance of immortalized VA10 cells cultured at air-liquid interface (ALI) was measured for the Example compounds 1, 2, 3, 5, 6, 7, 8, 9, 10, 11, 12, 14, 15, 16, 17, 18, 19, 20, 22, 23, 24, 25, 26, 27, 28, 29 and 30. In each case, the ratio between the TER in the presence of test compound and the TER in the presence of media+diluent alone was greater than 1.0. The ratio was greater than 2.0 for the Example compounds 1, 2, 5, 8, 9, 11, 12, 14, 15, 16, 17, 19, 20, 22, 23, 24, 25, 27 and 28. The ratio was greater than 3.0 for the Example compounds 2, 5, 9, 11, 16, 17, 19, 20, 22, 23, 24 and 25. These data show that the compounds of the invention enhance the barrier function of the epithelial cells.

The TER resistance of immortalized BCi-NS1.1 cells cultured at air-liquid interface (ALI) was measured for the Example compounds 1, 2, 3, 5, 6, 11, 12, 14, 16, 23, 24 and 25. The ratio between the TER in the presence of test compound and the TER in the presence of media+diluent alone was calculated. The ratio was greater than 2.0 for the Example compounds 1, 2, 11, 14, 16, 23 and 25. The ratio was greater than 3.0 for the Example compounds 1, 2, 11 and 16. These data show that the compounds of the invention enhance the barrier function of the epithelial cells.

Example C: Solubility and Stability

The solubility and the stability in plasma was measured for certain of the compounds. The methods were as follows:

Solubility in 10 mM Phosphate Buffer (pH 7.4):

The solubility sample testing of the compounds was performed by in phosphate buffer at pH 7.4 and using HPLC-MS detection. A stock solution of 10 M in DMSO was prepared for each compound. For the solubility test sample, 100 μL of the stock solution was diluted with 3.9 mL of a 10 mM phosphate buffer at pH 4.7 to a final concentration of 250 mM. The buffer solution was left to stand for 60 minutes at room temperature and then filtered. The filtrate was analyzed against two calibration points of the same analyte prepared at 250 mM and 25 mM using HPLC-MS. These calibration points were prepared from the same stock solution as the solubility sample by diluting it with DMSO:H2O (1:1) 1:40 and then again 1:10. The chromatographic signal area of the analyte in the solubility sample was then compared to the chromatographic signal area of the two calibration samples.

The chromatographic separation was performed on a Waters HPLC-MS system using a 50×2.1 mm xBridge $C_{18}$ column and a gradient elution of Water with 0.1% formic acid and acetonitrile with 0.1% formic acid. The analytes were analyzed in positive electro-spray mode using the $(M+H)^+$ in single ion recording.

Stability in Mouse and Human Plasma:

The stability of the compounds in mouse and human plasma was performed using protein precipitation as sample clean-up and HPLC-MS detection. The plasma stability studies of the compounds was performed at room temperature for up to 4 hours. A stock solution of 10M in DMSO was prepared for each compound. For the plasma stability samples, 100 μL of the stock solution was diluted with 3.9 mL of either mouse or human plasma to a final concentration of 250 mM. The plasma was left to equilibrate for 10 minutes at room temperature before the first analysis. For each analyzed time point (0, 30, 60, 120, 240 and 360 min) a 100 μL aliquot of the plasma was removed and protein precipitation (PPT) was performed on the aliquot by adding 900 μL of (ACN:DMSO) 95:5. The precipitated sample was shaken for 60 seconds and then centrifuged. The supernatant was transferred to an HPLC vial and analyzed using HPLC-MS. The chromatographic signal area of the samples at the different time points were then compared against each other, by setting the initial analysis at t=0 min as 100% and then calculating the %-value for each subsequent time point.

The chromatographic separation was performed on a Waters HPLC-MS system using a 50×2.1 mm xBridge $C_{18}$ column and a gradient elution of Water with 0.1% formic acid and acetonitrile with 0.100 formic acid. The analytes were analyzed in positive electro-spray mode using the $(M+H)^+$ in single ion recording.

The results are as follows:

| Example | Degradation in Human Plasma at RT % per hour | Degradation in Mouse Plasma at RT % per hour | MTS Solubility in Buffer (pH 7.4) μM |
|---|---|---|---|
| Azithromycin | 6 | | 0.26 |
| 2 | Stable | | 3.62 |
| 7 | Stable | | 0.23 |
| 12 | 2 | 2 | 0.30 |
| 16 | Stable | ca.15% | 0.03 |
| 17 | 20 | ca.20% | 0.66 |
| 18 | Stable | | 0.40 |
| 22 | Stable | Stable | 1.43 |
| 24 | Stable | Stable | 2.40 |
| 26 | Stable | 4 | 0.30 |
| 27 | Stable | 3 | 0.30 |
| 28 | Stable | Stable | 1.42 |
| 29 | 2 | Stable | 0.77 |
| 30 | Stable | Stable | 0.49 |

Example D: Barrier Integrity Enhancement in the Lung

The effect of compounds of the invention on maintenance of barrier integrity in the lungs of mice under sulphur dioxide insult was investigated.

Method:
1. 15 female mice were randomised into 3 groups of 5 mice. The three groups were:
   a) Control group
   b) Azithromycin treatment group
   c) Investigational compound treatment group
2. The mice were pre-treated for three days with:
   a) Placebo (Phosphate buffered saline—PBS) given at a dose of 10 mg/kg in an intravenous injection of 100 μl three times per week.
   b) Azithromycin: given at a dose of 10 mg/kg in an intravenous injection of 100 μl three times per week.
   c) The compound of Example 2: given at a dose of 10 mg/kg in an intravenous injection of 100 μl three times per week.
3. One mouse in each group was set to one side as a control. Four mice were then exposed to sulphur dioxide gas at a concentration of 200 ppm in air for a period of 60 minutes. The mice were in a cage that was inserted into a 45 L treatment box with a removable lid, a gas feed line and a gas exhaust vent. Gas was fed into the box at a rate that resulted in roughly 7 volume changes per hour. The gas was premixed from bottled air and bottled 200 ppm $SO_2$ in a first box and then fed into the treatment box. The level of $SO_2$ being fed into the treatment box can be varied by adjusting the relative flow of air and $SO_2$ from the two source cylinders. As the sulphur dioxide concentration in this experiment was 200 ppm, it was used neat, with no additional air being mixed with it. The mice had access to food and water for the duration of the treatment.

4. 24 hours after the end of the treatment, 1 mg of human serum albumin (HSA) in 100p saline was injected into the tail vein of each mouse, and fluorescent dextrans (FDs) were injected into the airways. The mice were then kept sedated for 90 minutes.

5. After 90 minutes, the mice were sacrificed via exsanguination. Plasma and bronchoalveolar lavage (BAL) were collected and the lungs were processed for paraffin embedding.

6. The level of HSA in the BAL was quantified by ELISA. The ELISA test used was the one commercially available from abcam (Human Serum Albumin kit ab179887). In line with the kit manufacturer's instructions, absorbance at 600 nm was measured. Fluorescent dextrans are quantified using a fluorescent plate reader.

The level of HSA that leaks into the lungs, as found in the BAL, is a measure of the integrity of the lung epithelial barrier.

Results:

In the placebo group, there were experimental difficulties with two of the four mice; in the Azithromycin group, there were experimental difficulties with one of the four mice; and in the investigational compound group, there were experimental difficulties with two of the four mice. Therefore, results were obtained from two mice in each of the placebo and investigational compound groups, and from three mice in the Azithromycin group. The HSA data read outs were as follows:

| Group | HSA level- absorbance at 600 nm | HSA level- absorbance at 600 nm relative to control |
| --- | --- | --- |
| PBS Control | 0.584 ± 0.175 | 1.000 ± 0.300 |
| Azithromycin | 0.346 ± 0.031 | 0.593 ± 0.053 |
| Example 2 | 0.373 ± 0.037 | 0.640 ± 0.058 |

The data are shown in the bar chart in FIG. 1.

It is seen that for both azithromycin and the compound of Example 2, the leakage of HSA into the lung following $SO_2$ insult, was reduced compared with the control. This indicates that azithromycin and the compound of Example 2 enhance the resilience of the barrier function of epithelial cells in the lung.

The invention claimed is:

1. A compound according to compound according to formula (I)

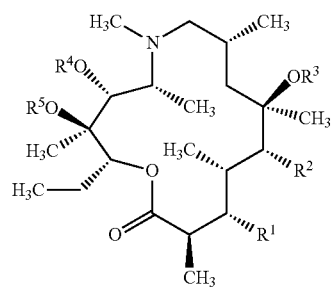

wherein $R^1$ is selected from the group consisting of carbamoyloxy, N—$C_{1-6}$-alkylcarbamoyloxy, N—($C_{6-14}$-aryl-$C_{1-6}$-alkyl)carbamoyloxy, N,N-di-$C_{1-6}$-alkylcarbamoyloxy, N,N-di-alkylcarbamoyloxy with the two alkyl substituents together forming a 5- to 8-membered heterocycle together with the nitrogen atom of the carbamate moiety, and $C_{1-6}$-alkylcarboxy;

and $R^2$ is according to formula (III)

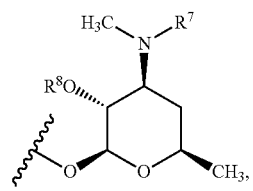

wherein $R^7$ is selected from the group consisting of $C_{1-6}$-alkyl, $C_{6-14}$-aryl-$C_{1-6}$-alkyl, $C_{3-6}$-alkylcarbonyl, $C_{6-14}$-arylcarbonyl, $C_{1-6}$-alkyl-$C_{6-14}$-arylcarbonyl, $C_{6-14}$-arylsulfonyl, $C_{1-6}$-alkyl-$C_{6-14}$-arylsulfonyl, $C_{6-14}$-aryl-$C_{1-6}$-alkylcarbonyl, $C_{6-14}$-aryl-O—$C_{1-6}$-alkylcarbonyl, $C_{6-14}$-aryl-$C_{1-6}$-alkyl-O—$C_{1-6}$-alkyl-carbonyl, HOOC—$(CH_2)_m$-(CO)- with m being from 0 to 6, a substituent of formula (V.1)

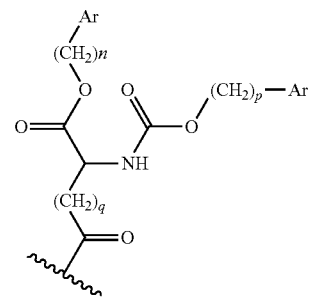

with Ar being $C_{6-14}$-aryl and n, p and q being independently from 0 to 6,
$C_{6-14}$-aryl-$C_{1-6}$-alkyl-O—CO—NH—$C_{1-6}$-alkyl-CO—, and
$C_{6-14}$-arylsulfonyl, and $C_{1-6}$-alkyl-$C_{6-14}$-arylsulfonyl, whereby alkyl and/or aryl in $R^7$ is optionally substituted by 1 to 6 halogen and/or CN; and
$R^8$ is selected from the group consisting of H; $C_{6-14}$-arylcarbonyl optionally substituted with 1 to 5 groups selected from halogen atoms, $C_{1-3}$-alkyl sulfonyl groups, $C_{1-3}$-alkyl groups and/or $C_{1-3}$-alkoxy groups; $C_{3-6}$-alkylcarbonyl; HOOC—$(CH_2)_m$-(CO)- with m being from 0 to 6, a substituent of formula (V.1) as depicted hereinbefore with Ar being $C_{6-14}$-aryl and n, p and q being independently from 0 to 6; and heteroarylcarbonyl having a 5- to 10-membered ring containing 1, 2 or 3 heteroatoms selected from the group consisting of O, N and S, the ring of the heteroarylcarbonyl optionally being substituted by 1 to 3 substituents selected from the group consisting of $C_{1-4}$-alkyl, $C_{1-4}$-alkoxy, $C_{2-4}$-alkenyl, $C_{2-4}$-alkenoxy, halogen and CN, whereby alkyl and/or aryl in $R^8$ is optionally substituted by 1 to 6 halogen and/or CN;
$R^3$ is H; and
$R^4$ and $R^5$ are independently selected from H and $C_{1-6}$-alkylcarbonyl, whereby alkyl is optionally substituted by 1 to 6 halogen and/or CN;
and
or a pharmaceutically acceptable ester, amide, carbamate, solvate or salt thereof, including a salt of such an ester, amide or carbamate, and a solvate of such an ester, amide, carbamate or salt.

2. The compound according to claim 1, wherein $R^1$ is selected from the group consisting of $C_{1-3}$-alkylcarboxy, and a moiety according to formula (IV)

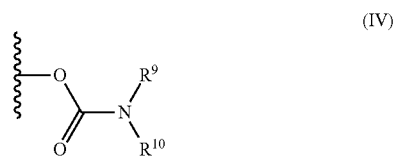

(IV)

wherein $R^9$ and $R^{10}$ are independently selected from the group consisting of H, $C_{1-3}$-alkyl and $C_{6-10}$-aryl-$C_{1-3}$-alkyl or are together alkyl forming a 5- or 6-membered aliphatic heterocycle together with the nitrogen atom they are both bonded to, whereby said heterocycle optionally contains one or two further heteroatom(s) selected from the group consisting of N, O and S, or said heterocycle is selected from the group consisting of piperidine, piperazine and morpholin,
whereby alkyl, aryl and/or the heterocycle in $R^1$ is optionally substituted by 1 to 6 halogen and/or CN.

3. The compound according to claim 1, wherein
$R^7$ is selected from the group consisting of $C_{1-3}$-alkyl, $C_{6-10}$-aryl-$C_{1-3}$-alkyl, linear or branched $C_{3-4}$-alkylcarbonyl, $C_{6-10}$-arylcarbonyl, $C_{6-10}$-aryl-$C_{1-3}$-alkylcarbonyl, $C_{6-10}$-aryl-O—$C_{1-3}$-alkylcarbonyl, $C_{6-10}$-aryl-$C_{1-3}$-alkyl-O—$C_{1-3}$-alkyl-carbonyl, HOOC—$(CH_2)_m$-(CO)-with m being from 0 to 3, a moiety according to formula (V.2)

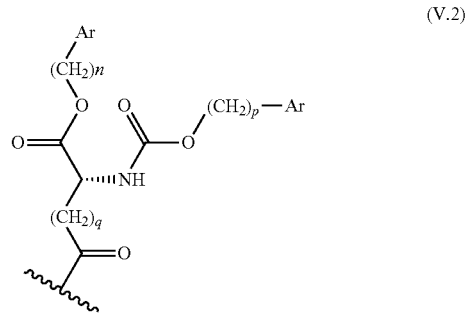

(V.2)

wherein Ar is $C_{6-10}$-aryl and n, p and q each are independently from 0 to 3,
$C_{6-10}$-aryl-$C_{1-3}$-alkyl-O—CO—NH—$C_{1-3}$-alkyl-CO—, $C_{6-10}$-arylsulfonyl, and $C_{1-3}$-alkyl-$C_{6-10}$-arylsulfonyl; and
$R^8$ is selected from the group consisting of H, $C_{6-10}$-arylcarbonyl, $C_{6-10}$-arylcarbonyl substituted with 1 to 3 halogen atoms, $C_{1-2}$-alkyl groups and/or $C_{1-2}$-alkoxy groups, linear or branched, $C_{3-4}$-alkylcarbonyl, HOOC—$(CH_2)_m$-(CO)- with m being from 0 to 3,
a moiety according to formula (V.2) as depicted hereinbefore wherein Ar is $C_{6-10}$-aryl and n, p and q each are independently from 0 to 3,
$C_{1-3}$-alkylsulfonyl-bi-$C_{6-10}$-aryl-carbonyl, and
heteroarylcarbonyl having a 5-, 6- or 10-membered ring containing 1, 2 or 3 heteroatoms, with the heteroatom(s) in each case being selected from the group consisting of N, O and S, the ring of the heteroarylcarbonyl optionally being substituted by 1 or 2 substituents selected from the group consisting of $C_{1-2}$-alkyl, $C_{1-2}$-alkoxy, $C_{2-3}$-alkenyl, $C_{2-3}$-alkenoxy, halogen and CN;
whereby alkyl, aryl and/or the heterocycle in $R^8$ is optionally substituted by 1 to 6 halogen and/or CN.

4. The compound according to claim 1, wherein
$R^1$ is N—($C_{6-14}$-aryl-$C_{1-6}$-alkyl)carbamoyloxy, N,N-dialkylcarbamoyloxy with the two alkyl substituents together forming a 5- to 8-membered heterocycle together with the nitrogen atom of the carbamate moiety and $C_{1-6}$alkylcarboxy;
$R^7$ is selected from the group consisting of $C_{1-3}$-alkyl, a moiety according to formula (V.2) wherein Ar is phenyl, n and p each are the same and 1 or 2 and q is 2 or 3, phenyl-$C_{1-2}$-alkyl-O—CO—NH—$C_{1-2}$-alkyl-CO— and phenyl-O—$C_{1-3}$-alkylcarbonyl, whereby alkyl, aryl and/or the heterocycle in $R^7$ is optionally substituted by 1 to 3 halogen and/or CN; and
$R^8$ is selected from the group consisting of H, HOOC—$(CH_2)_m$-(CO)- with m being from 1 to 3, benzoyl, methylbenzoyl, ethylbenzoyl, methoxybenzoyl, ethoxybenzoyl, methylsulfonylphenylbenzoyl and naphthylcarbonyl, whereby alkyl, aryl and/or the heterocycle in $R^8$ is optionally substituted by 1 to 3 halogen and/or CN.

5. The compound according to claim 1, wherein
$R^1$ is N—($C_{6-14}$-aryl-$C_{1-6}$-alkyl)carbamoyloxy, N,N-dialkylcarbamoyloxy with the two alkyl substituents together forming a 5- to 8-membered heterocycle together with the nitrogen atom of the carbamate moiety and $C_{1-6}$alkylcarboxy;
$R^2$ is according to formula (III)

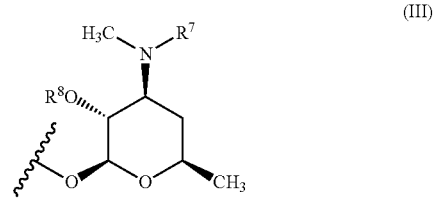

(III)

wherein
$R^7$ is $C_{1-6}$-alkyl; and
$R^8$ is selected from the group consisting of $C_{6-14}$-arylcarbonyl optionally substituted with 1 to 5 groups selected from $C_{1-3}$-alkyl sulfonyl groups and/or $C_{1-3}$-alkyl groups; HOOC—$(CH_2)_m$-(CO)- with m being from 0 to 6, a substituent of formula (V.1)

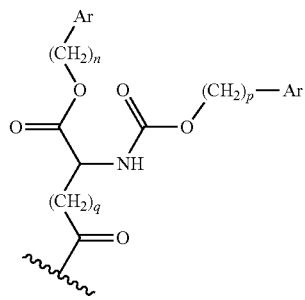

with Ar being $C_{6-14}$-aryl and n, p and q being independently from 0 to 6;
$R^3$ is H; and
$R^4$ and $R^5$ are both H;
or a pharmaceutically acceptable ester, amide, carbamate, solvate or salt thereof, including a salt of such an ester, amide or carbamate, and a solvate of such an ester, amide, carbamate or salt.

6. The compound according to claim 1, which is selected from the group consisting of
 (3aR,4R,7R,8S,9S, 10R, 11S, 13R, 16R, 16aR)-10-{[(2S, 3R,4S,6R)-3-(benzoyloxy)-4-(dimethylamino)-6-methyloxan-2-yl]oxy}-4-ethyl-11-hydroxy-3a, 7,9,11, 13, 15, 16-heptamethyl-2,6-dioxo-tetradecahydro-2H-[1,3]dioxolo[4,5-c]1-oxa-6-azacyclopentadecan-8-yl morpholine-4-carboxylate (Example 3);
 (2S,3R,4S,6R)-2-{[(3aR,4R,7R,8S,9S, 10R, 11S, 13R, 16R, 16aR)-8-[(benzylcarbamoyl)oxy]-4-ethyl-11-hydroxy-3a,7,9,11,13,15,16-heptamethyl-2,6-dioxo-tetradecahydro-2H-[1,3]dioxolo[4,5-c]1-oxa-6-azacyclopentadecan-10-yl]oxy}-4-(dimethylamino)-6-methyloxan-3-yl benzoate (Example 4);
 (2R,3S,4R,5R,8R, 10S, 11R, 12S, 13S, 14R)-11-{[(2S, 3R,4S,6R)-4-[benzyl(methyl)amino]-3-hydroxy-6-methyloxan-2-yl]oxy}-2-ethyl-3,4,10-trihydroxy-13-{ [(4R,5S,6S)-5-hydroxy-4-methoxy-4,6-dimethyloxan-2-yl]oxy}-3,5,6,8, 10, 12, 14-heptamethyl-1-oxa-6-azacyclopentadecan-15-one (Example 5);
 N-[(2S,3R,4S,6R)-2-{[(2R,3S,4R,5R,8R,10S,11R,12S, 13S, 14R)-2-ethyl-3,4, 10-trihydroxy-13-{[(4R,5S, 6S)-5-hydroxy-4-methoxy-4,6-dimethyloxan-2-yl]oxy}-3,5,6,8,10,12, 14-heptamethyl-15-oxo-1-oxa-6-azacyclopentadecan-11-yl]oxy}-3-hydroxy-6-methyloxan-4-yl]-N-methylbenzamide (Example 6);
 N-[(2S,3R,4S,6R)-2-{[(2R,3S,4R,5R,8R, 10S, 11R, 12S, 13S, 14R)-2-ethyl-3,4,10-trihydroxy-13-{[(4R,5S,6S)-5-hydroxy-4-methoxy-4,6-dimethyloxan-2-yl] oxy}-3, 5,6,8,10,12,14-heptamethyl-15-oxo-1-oxa-6-azacyclopentadecan-11-yl]oxy}-3-hydroxy-6-methyloxan-4-yl]-N-methylnaphthalene-2-sulfonamide (Example 8);
 N-[(2S,3R,4S,6R)-2-{[(2R,3S,4R,5R,8R, 10S, 11R, 12S, 13S, 14R)-2-ethyl-3,4,10-trihydroxy-13-{[(4R,5S,6S)-5-hydroxy-4-methoxy-4,6-dimethyloxan-2-yl]oxy}-3, 5,6,8,10,12, 14-heptamethyl-15-oxo-1-oxa-6-azacyclopentadecan-11-yl]oxy}-3-hydroxy-6-methyloxan-4-yl]-N,4-dimethylbenzene-1-sulfonamide (Example 10);
 (2S,3R,4S,6R)-2-{[(2R,3R,4R,5R,8R, 10S, 11R, 12S, 13S, 14R)-4, 13-bis(acetyloxy)-2-ethyl-3,10-dihydroxy-3,5,6,8,10,12,14-heptamethyl-15-oxo-1-oxa-6-azacyclopentadecan-11-yl]oxy}-4-(dimethylamino)-6-methyloxan-3-yl benzoate (Example 11).

7. A pharmaceutical composition comprising at least one compound of Formula (Ia) and at least one pharmaceutically acceptable excipient:

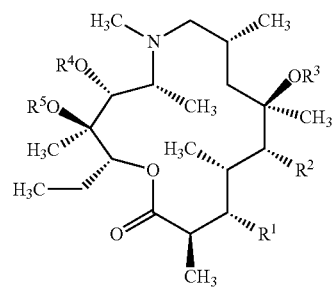

wherein
$R^1$ is selected from the group consisting of carbamoyloxy, N—$C_{1-6}$-alkylcarbamoyloxy, N—($C_{6-14}$-aryl-$C_{1-6}$-alkyl)carbamoyloxy, N,N-di-$C_{1-6}$-alkylcarbamoyloxy, N,N-di-alkylcarbamoyloxy with the two alkyl substituents together forming a 5- to 8-membered heterocycle together with the nitrogen atom of the carbamate moiety, and $C_{1-6}$-alkylcarboxy;
and
$R^2$ is according to formula (III)

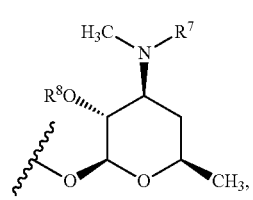

wherein
$R^7$ is selected from the group consisting of $C_{1-6}$-alkyl,
and
$R^8$ is selected from the group consisting of H; $C_{6-14}$-arylcarbonyl optionally substituted with 1 to 5 groups selected from halogen atoms, $C_{1-3}$-alkyl sulfonyl groups, $C_{1-3}$-alkyl groups and/or $C_{1-3}$-alkoxy groups; $C_{3-6}$-alkylcarbonyl; HOOC—$(CH_2)_m$-(CO)- with m being from 0 to 6, a substituent of formula (V.1) as depicted hereinbefore with Ar being $C_{6-14}$-aryl and n, p and q being independently from 0 to 6; and heteroarylcarbonyl having a 5- to 10-membered ring containing 1, 2 or 3 heteroatoms selected from the group consisting of O, N and S, the ring of the heteroarylcarbonyl optionally being substituted by 1 to 3 substituents selected from the group consisting of $C_{1-4}$-alkyl, $C_{1-4}$-alkoxy, $C_{2-4}$-alkenyl, $C_{2-4}$-alkenoxy, halogen and CN, whereby alkyl and/or aryl in $R^8$ is optionally substituted by 1 to 6 halogen and/or CN;
$R^3$ is H; and
$R^4$ and $R^5$ are independently selected from H and $C_{1-6}$-alkylcarbonyl, whereby alkyl is optionally substituted by 1 to 6 halogen and/or CN;
or a pharmaceutically acceptable ester, amide, carbamate, solvate or salt thereof, including a salt of such an ester, amide or carbamate, and a solvate of such an ester, amide, carbamate or salt.

8. A method for the treatment of a disease or condition that benefits from enhancement or restoration of epithelial barrier function, said method comprising administering to a mammal a therapeutically effective amount of the compound of claim 1.

9. The method according to claim 8, wherein the disease or condition is an airways disease and the epithelial tissue is in the respiratory tract epithelial tissue.

10. The method according to claim 8 wherein the condition is asthma, chronic obstructive pulmonary disease (COPD), Cystic Fibrosis (CF), non-CF Bronchiectasis, chronic rhinosinusitis, diffuse panbronchiolitis (DPB), chronic bronchitis, Bronchiolitis Obliterans Organizing Pneumonia (BOOP) primary or secondary to chemotherapy or post-transplantation status, infantile respiratory distress syndrome (IRDS) and its long term complication, bronchopulmonary dysplasia, neuromuscular respiratory depression and/or failure, pneumonia and conditions caused by and associated with Respiratory Syncytial Virus (RSV) and related viruses.

11. The method according to claim 8 wherein the treatment of a disease or disorder is systemic inflammatory distress syndrome (SIRS), adult respiratory distress syndrome (ARDS), inflammatory bowel disease, ulcerative colitis or Crohn's disease.

12. A method for the treatment or prophylaxis of a disease or condition that benefits from enhancement or restoration of epithelial barrier function, which comprises administering to the mammal a therapeutically effective amount of a compound or composition as defined in claim 1.

\* \* \* \* \*